United States Patent
Ormsby et al.

(10) Patent No.: US 7,004,938 B2
(45) Date of Patent: Feb. 28, 2006

(54) RADIO-FREQUENCY-BASED CATHETER SYSTEM WITH IMPROVED DEFLECTION AND STEERING MECHANISMS

(75) Inventors: Theodore C. Ormsby, Milpitas, CA (US); Ming-Fan Law, San Diego, CA (US); George L. Leung, San Diego, CA (US)

(73) Assignee: MedWaves, Inc., San Diego, CA (US)

(*) Notice: Subject to any disclaimer, the term of this patent is extended or adjusted under 35 U.S.C. 154(b) by 157 days.

(21) Appl. No.: 10/306,757

(22) Filed: Nov. 27, 2002

(65) Prior Publication Data

US 2003/0114844 A1 Jun. 19, 2003

Related U.S. Application Data

(60) Provisional application No. 60/334,199, filed on Nov. 29, 2001.

(51) Int. Cl.
*A61B 18/18* (2006.01)
(52) U.S. Cl. .................. 606/33; 607/156; 607/101; 606/34
(58) Field of Classification Search ............. 606/41, 606/32–34, 47, 129, 50, 4; 607/96, 101, 607/115, 116, 152, 154, 156, 100
See application file for complete search history.

(56) References Cited

U.S. PATENT DOCUMENTS

| | | | |
|---|---|---|---|
| 2,847,990 A | 8/1958 | Ayre | |
| 3,058,473 A | 10/1962 | Whitehead | |
| 3,521,620 A | 7/1970 | Cook | 128/2.05 |
| 3,552,384 A | 1/1971 | Pierie et al. | 128/2.05 |
| 4,723,936 A | 2/1988 | Buchbinder et al. | 604/95 |
| 4,906,230 A | 3/1990 | Maloney et al. | 604/95 |
| 4,960,134 A | 10/1990 | Webster, Jr. | 128/786 |
| 5,843,076 A | 12/1998 | Webster, Jr. et al. | 606/41 |
| 5,857,997 A | 1/1999 | Cimino et al. | 604/95 |
| 5,863,291 A | 1/1999 | Schaer | 606/41 |
| 5,876,373 A | 3/1999 | Giba et al. | 604/95 |
| 5,882,333 A | 3/1999 | Schaer et al. | 604/95 |
| 5,897,529 A | 4/1999 | Ponzi | 604/95 |
| 5,904,667 A | 5/1999 | Falwell | 604/95 |
| 5,916,241 A * | 6/1999 | Rudie et al. | 607/101 |
| 6,071,280 A | 6/2000 | Edwards et al. | 606/41 |
| 6,183,463 B1 | 2/2001 | Webster, Jr. | 604/528 |
| 6,254,568 B1 | 7/2001 | Ponzi | 604/95 |
| 6,267,746 B1 | 7/2001 | Bumbalough | 604/95.01 |
| 6,356,790 B1 | 3/2002 | Maguire et al. | 607/102 |
| 6,383,182 B1 | 5/2002 | Berube et al. | 606/33 |
| 6,500,167 B1 | 12/2002 | Webster, Jr. | 604/528 |
| 6,663,622 B1 * | 12/2003 | Foley et al. | 606/34 |
| 6,669,692 B1 * | 12/2003 | Nelson et al. | 606/41 |
| 2002/0087151 A1 * | 7/2002 | Mody et al. | 606/15 |

* cited by examiner

*Primary Examiner*—Rosiland Rollins
(74) *Attorney, Agent, or Firm*—Stephen C. Beurele; Procopio Cory Hargreaves & Savitch LLP

(57) ABSTRACT

A RF catheter system includes a catheter with a proximal portion, a distal portion having a distal end and a lumen extending from the proximal portion to the distal portion. Inner and outer coaxially aligned conductors extend within the catheter and are coaxial with the lumen. A deflectable catheter guide is disposed within the catheter lumen and extends proximally within the catheter lumen and terminates distally of the distal end of the catheter to define a biological ablation pathway. A radio-frequency antenna is disposed at the distal portion of the catheter and is in electrical communication with the inner and outer coaxially aligned conductors. The radio-frequency antenna is adaptable to receive and transmit radio-frequency energy for ablating biological tissue along the ablation pathway.

18 Claims, 13 Drawing Sheets

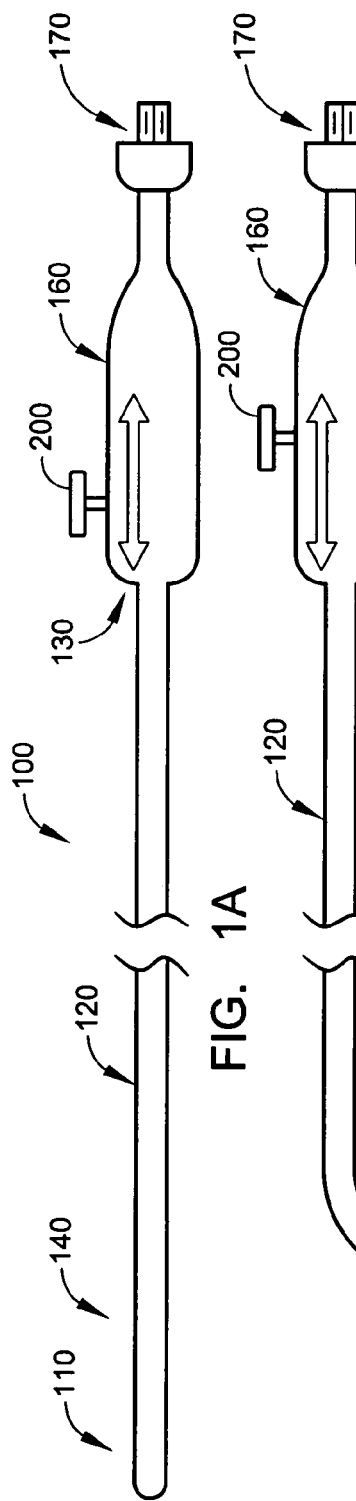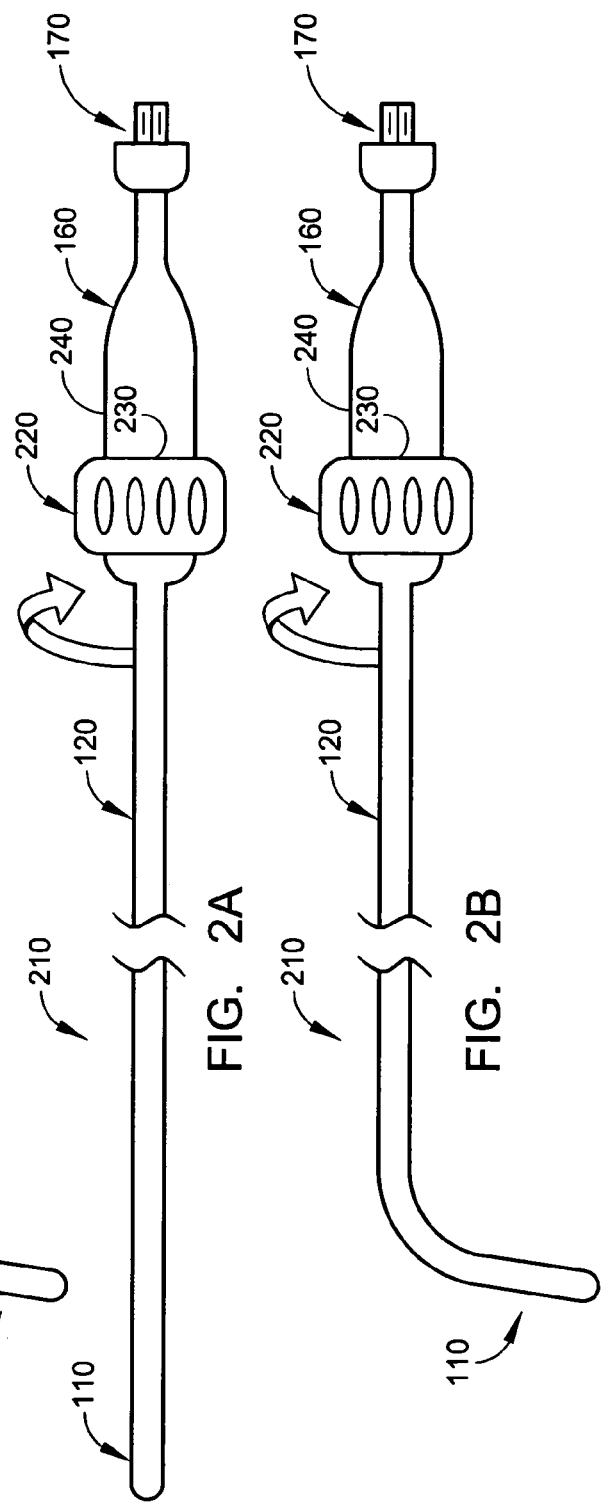

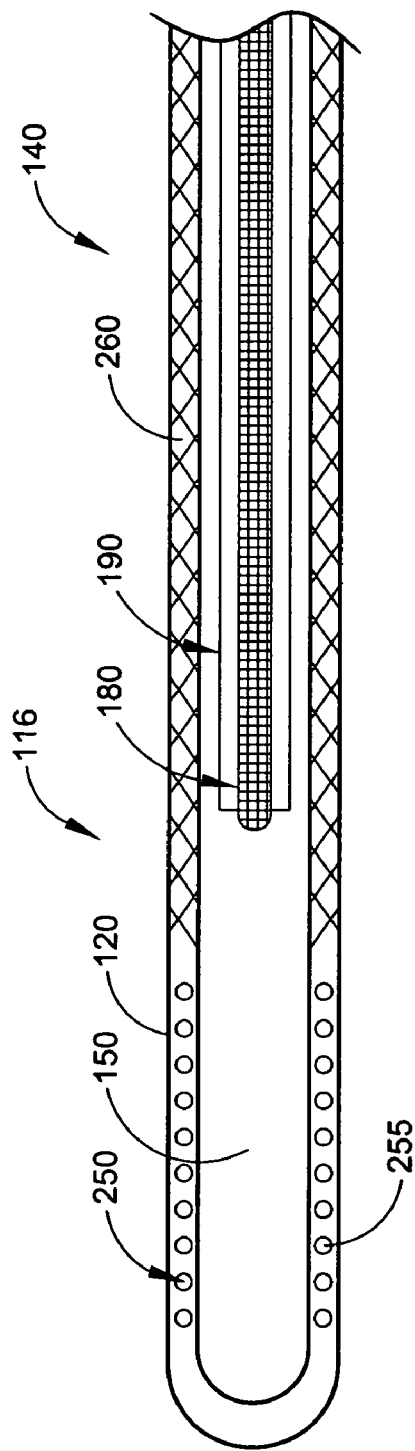
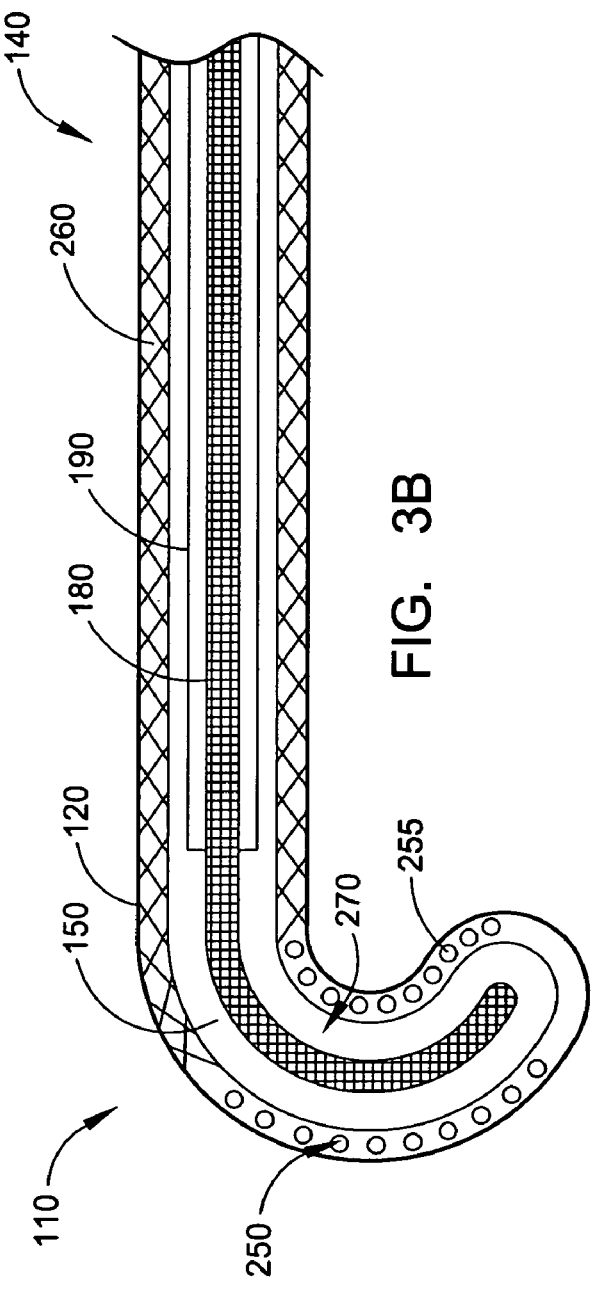
FIG. 3A
FIG. 3B

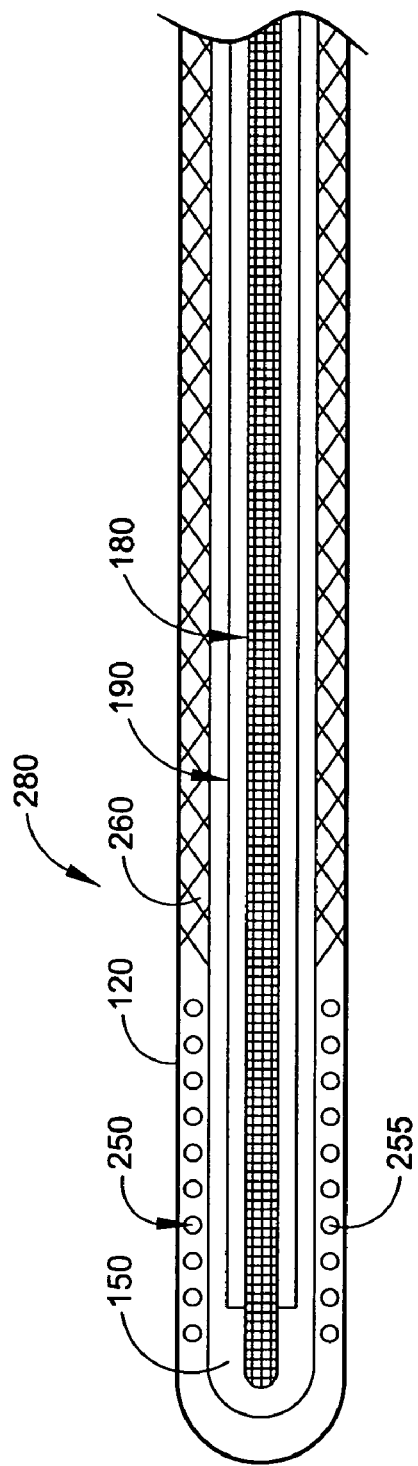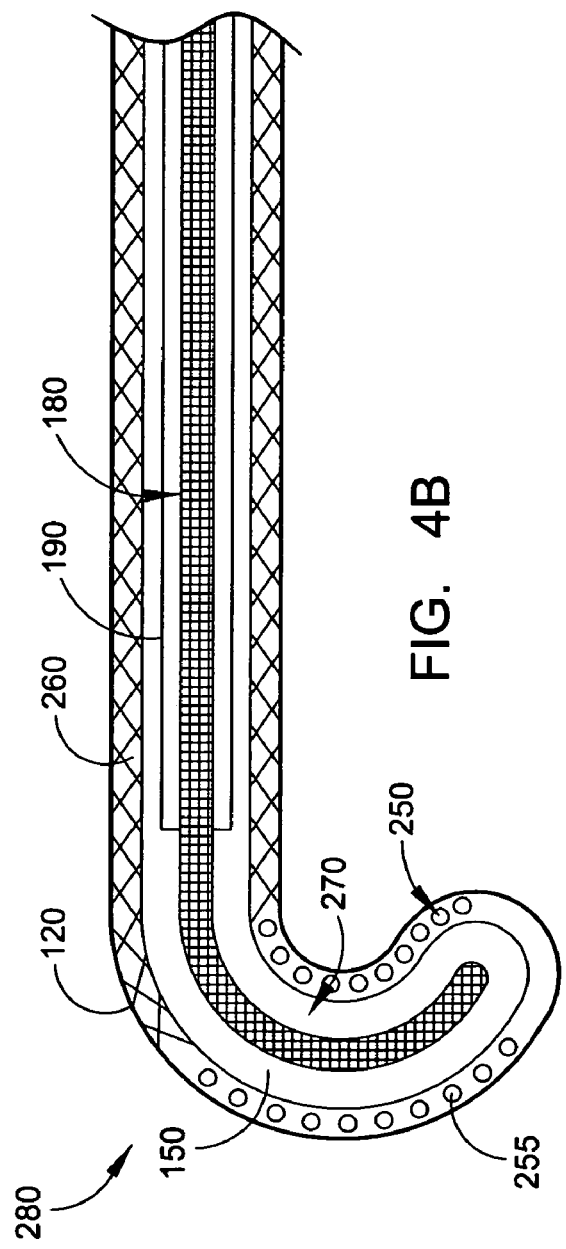

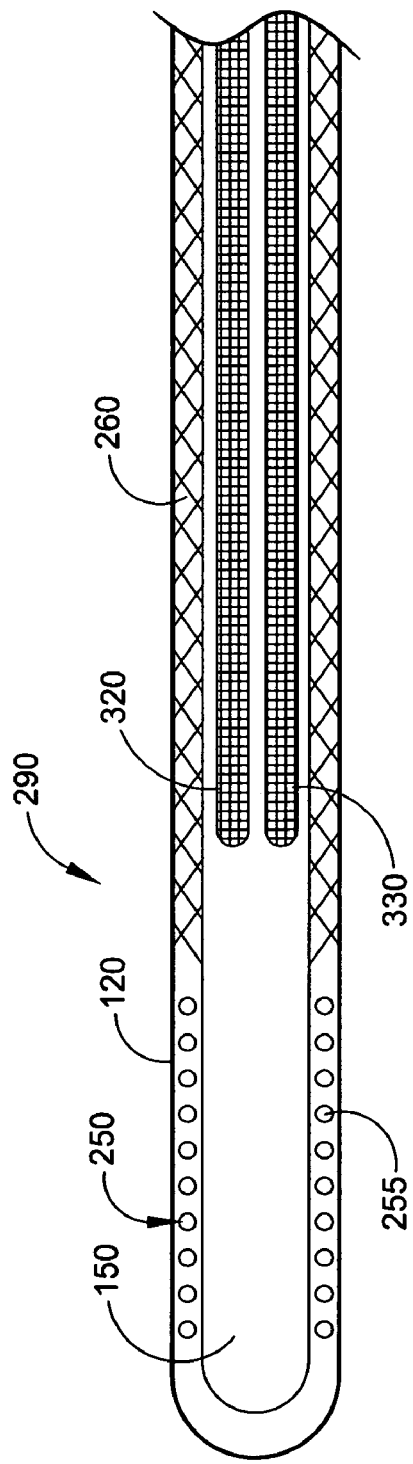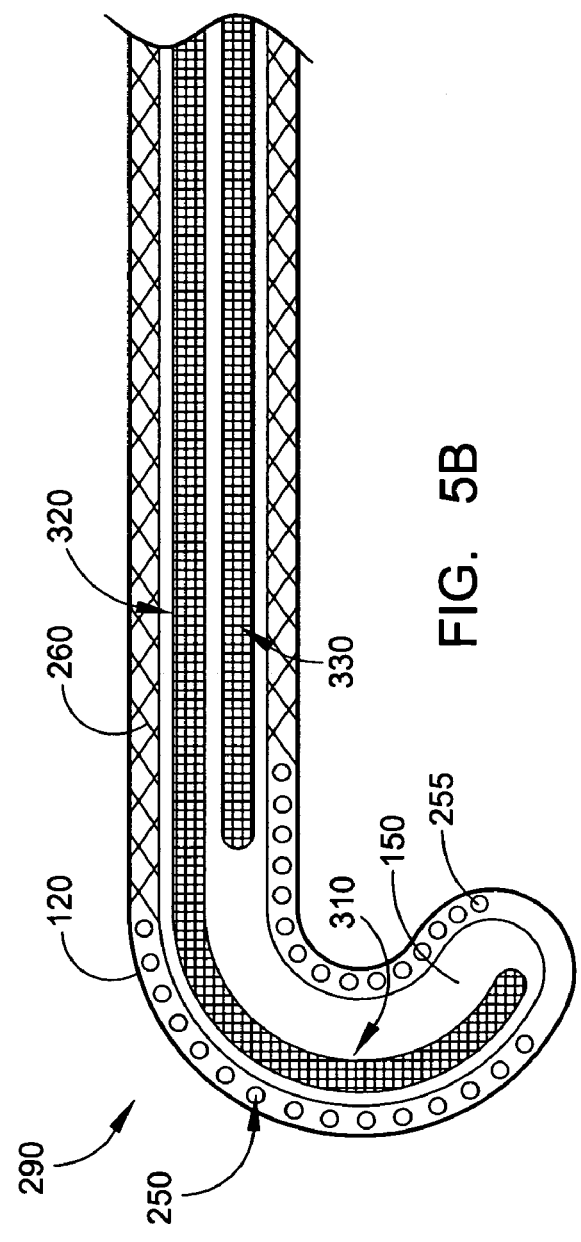
FIG. 5A
FIG. 5B

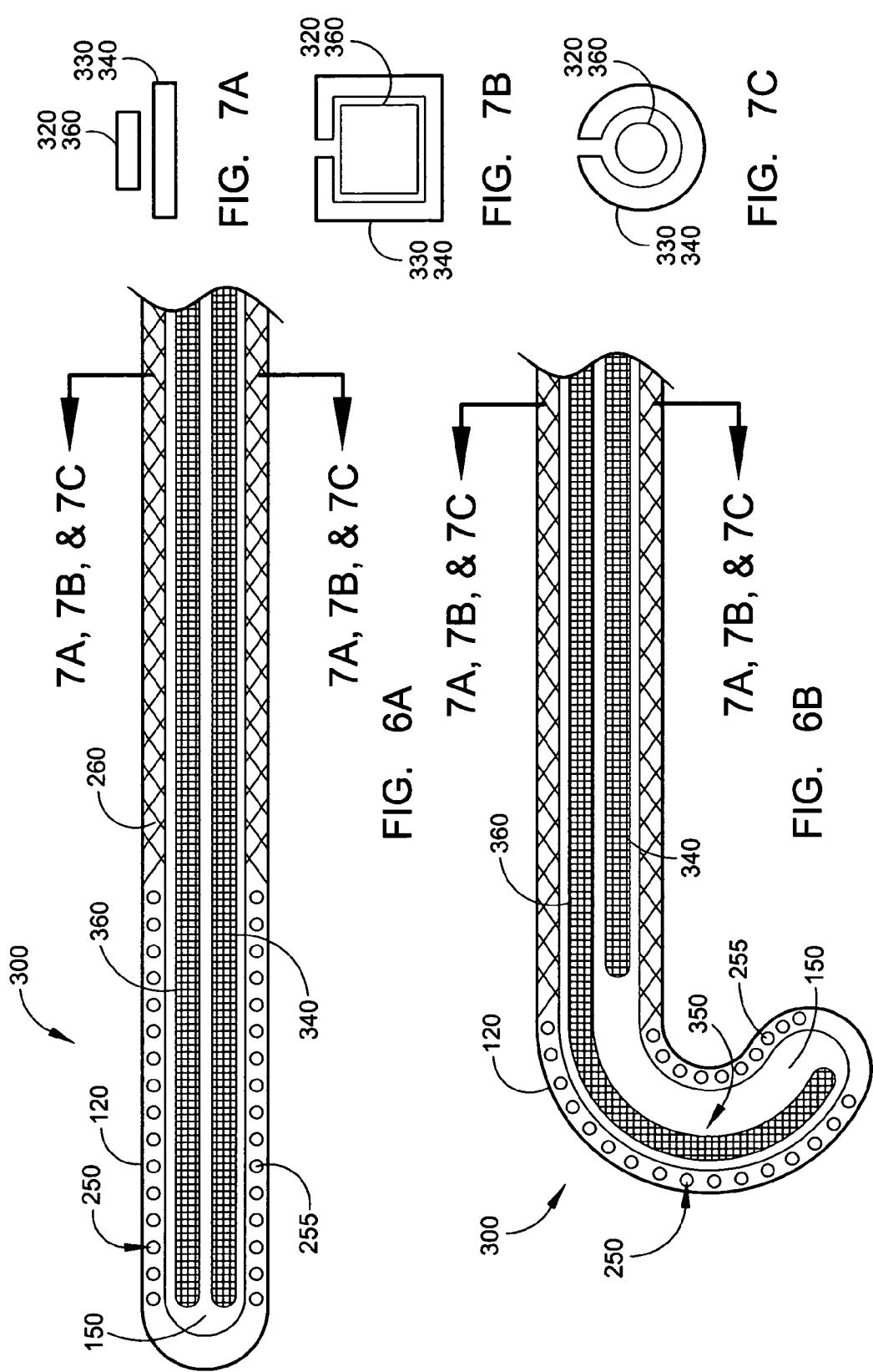

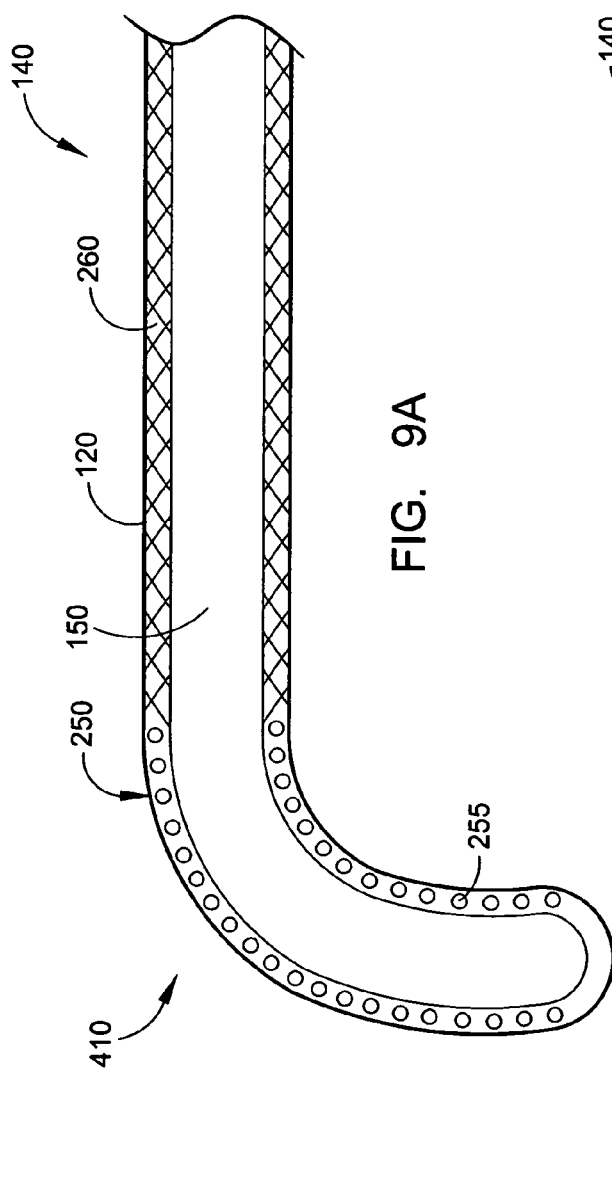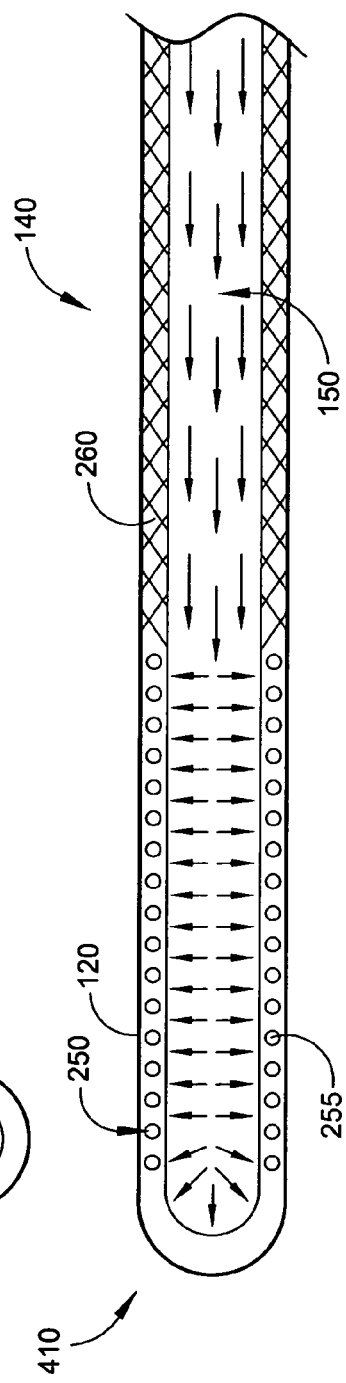

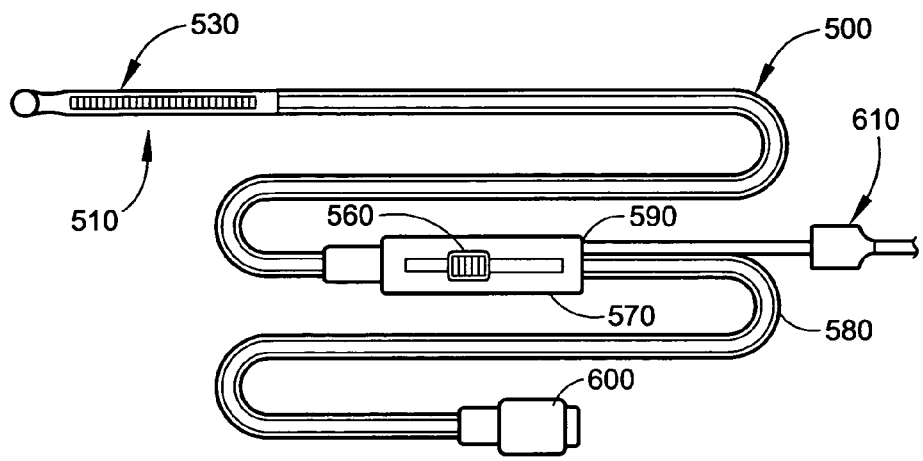
FIG. 10
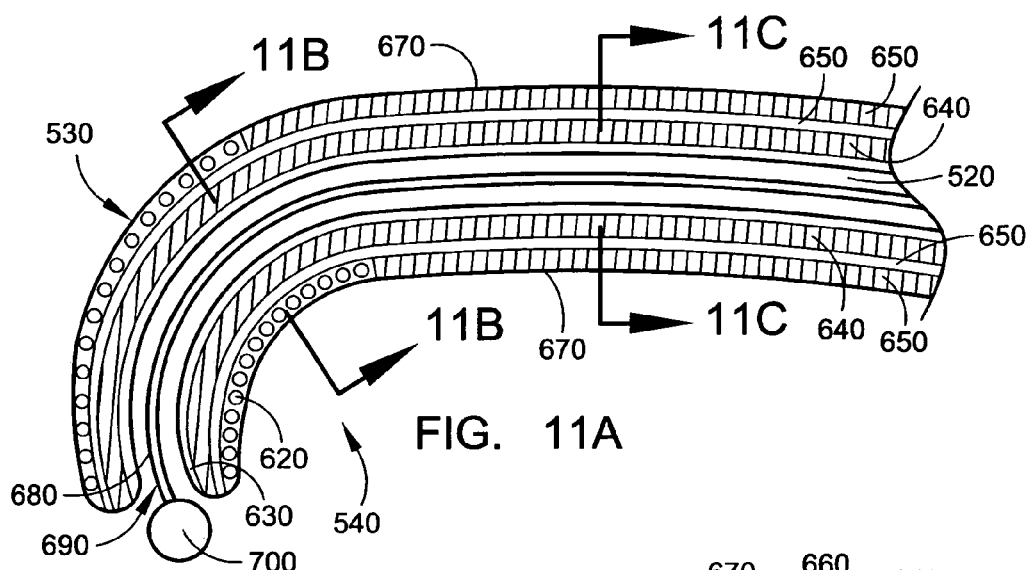
FIG. 11A
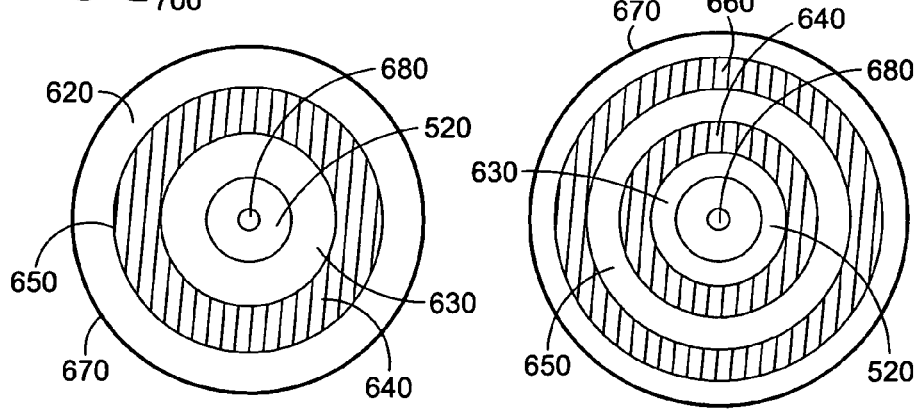
FIG. 11B
FIG. 11C

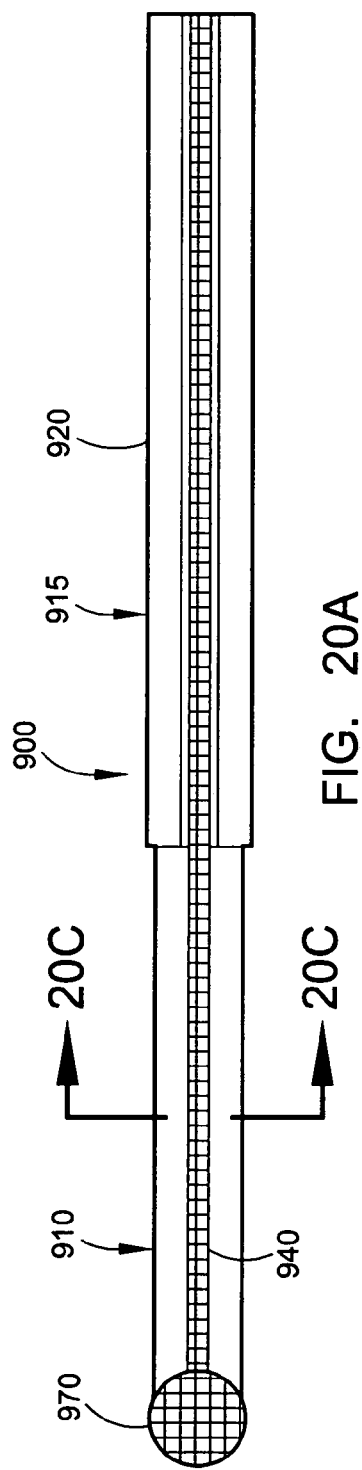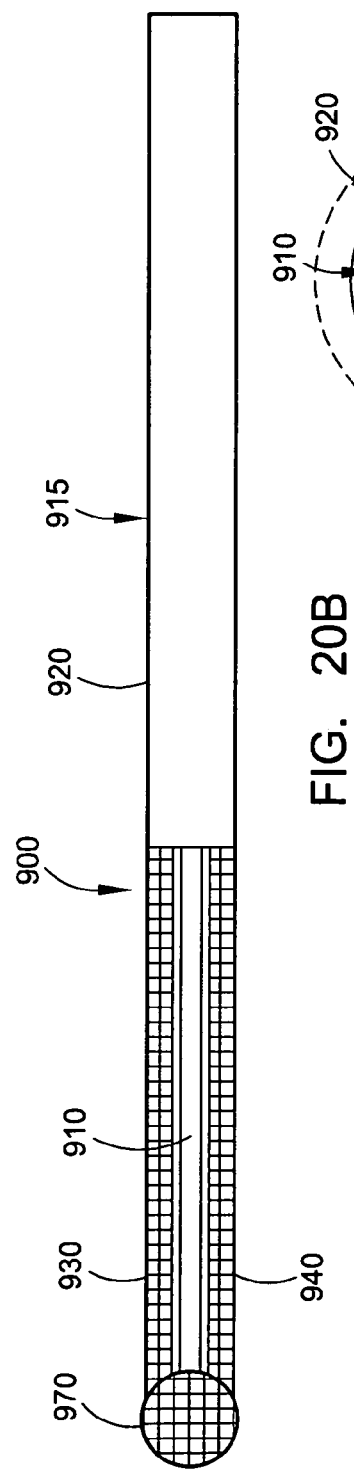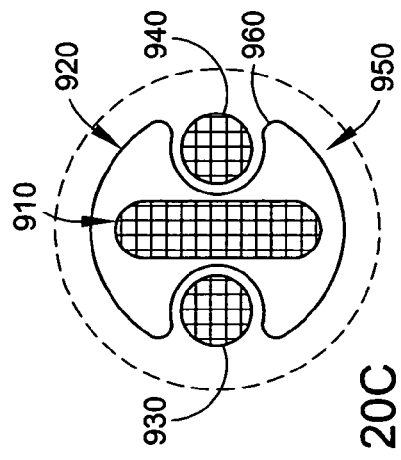

RADIO-FREQUENCY-BASED CATHETER SYSTEM WITH IMPROVED DEFLECTION AND STEERING MECHANISMS

The present application claims the benefit of provisional application 60/334,199 filed Nov. 29, 2001.

FIELD OF THE INVENTION

The present invention relates, in general, to radio-frequency ("RF") or microwave powered medical apparatus and ablation of biological tissues, and, in particular, to a RF based catheter system with improved deflectable and steering capabilities.

BACKGROUND OF THE INVENTION

In recent years medical devices have gained significant acceptance in the medical community as an important treatment modality for heart diseases and other serious ailments, which were traditionally remedied by medication or surgical operation. Two fundamental trends have emerged in the treatment of cardiac diseases. The first has been the shift from open-heart surgical procedures to less invasive and less expensive catheter-based treatments, which are safer and less debilitating.

The second trend is represented by the shift from the use of anti-arrhythmic drugs to minimally invasive catheters or other device-based therapies to palliate incurable arrhythmias. For example, automatic cardioverter-defibrillator are routinely implanted in patients with lethal ventricular arrhythmias to reduce the likelihood of sudden death. Thus, radio-frequency (ns"RF") catheter ablation is now being performed in large number of patients suffering from cardiac arrhythmias.

Despite these advances in technology, atrial fibrillation ("AF") remains a significant challenge. AF, a rapid irregular rhythm in the atria or upper chambers of the heart induced by non-uniformed electrical pulses, represents a leading cause of stroke and heart attack and a major health care burden. To date, the most effective surgical procedure for the treatment of AF has been the Maze procedure undertaken in "open-heart" surgery. In the Maze procedure, incisions are made along pre-determined lines exterior of the atrium, which are then sutured together. As healing develops, scars are formed along the incision lines thereby forming barriers to the conduction of electrical impulses. By creating such barriers, AF can no longer be sustained and regular heart rhythm is restored. However, the Maze procedure has not been widely adopted due to the cost and mortality associated with open-heart surgery, but only as adjunct to other major procedures such as mitral-valve replacement.

One new approach to mimic the Maze operation is represented by catheter-based radio-frequency ablation technique, wherein, instead of surgical incisions, a catheter-antenna is applied to destroy or ablate the heart tissues inside the atrial chamber. The catheter-antenna is passed through the vein for access to the atrium, as commonly practiced in the medical field. Within the atrium, the tip of the catheter-antenna is positioned, usually with the aid of x-ray or fluoroscopic means, and is brought into contact with the heart tissue at a desired location or spot where ablation is required. At this spot, the tissue is destroyed by resistive heating generated from the catheter-antenna. Thereafter, the catheter-antenna is re-positioned to the next spot for ablation. A series of spot ablations thus mimics the linear lesions as accomplished under the Maze procedure against the conduction of electrical impulses.

Existing catheter-based ablation procedures are recognizably less intrusive than "open-heart" surgery. In addition, during the ablation, disruption of cardiovascular function is reduced. However, a successful catheter-based radio-frequency ablation procedure requires the ablation of tissue spots within the spatial or proximity tolerance between adjacent spots, usually less than 2 millimeters, to prevent the passage of electrical impulses. In that connection, the task for the precise placement of the catheter-antenna represents a critical element of a successful procedure.

A major drawback of such existing procedures is in the time-consuming task in positioning the catheter-antenna at the desired ablation spots within the atrium while the heart chamber muscles are pulsating. Movements of atrial wall or the heart muscles often render accurate placement of the catheter-antenna difficult, and slippage of the catheter-antenna tends to occur thereby damaging portions of the atrium where ablation is not desired. As a result, placement of the catheter based RF ablation cannot be efficiently accomplished, and prolonged procedure time, in excess of 12 hours, can be expected. Further, during the procedure, x-ray or other irradiating means are routinely employed for locating and positioning the catheter-antenna, which dictates the use of heavy lead protective gear by the electro-physiologist. As a result, such inconvenience is often amplified by the prolonged procedure time, which detracts from the use of catheter-based antenna as an efficient means for tissue ablation.

To minimize the risk of slippage, for example, in U.S. Pat. No. 5,741,249, a catheter-based microwave antenna is disclosed wherein a distal tip is incorporated into the antenna to anchor it to the atrial wall. However, while this design reduces the likelihood of antenna or catheter-antenna slippage during each ablation step, it does not eliminate the consuming task to secure precise placement of the antenna along the desired ablation path for each ablation step. Thus, after each ablation step, the antenna has to be re-positioned and anchored precisely at the next spot which must be located within the spatial or proximity tolerance on the ablation path as referenced above.

Accordingly, effective treatments for atrial fibrillation with catheter ablation will require the creation of long or overlapping linear or curvilinear ablation lesions on the inner surface of the atrium. These lesions can then act as barriers to the conduction of electrical impulses, thus preventing atrial fibrillation.

A critical requirement for the effective catheter-based ablation of atrial fibrillation is the ability to stabilize and anchor the catheter and microwave antenna inside the atrial chambers. New catheter ablation systems capable of stabilizing and anchoring the catheter and microwave antenna inside the atrial chambers, preferably capable of producing long or overlapping linear or curvilinear ablation lesions, are required for the development of minimally invasive catheter-based curative procedures for atrial fibrillation.

U.S. Pat. No. 6,190,382, issued Feb. 20, 2001 and U.S. patent application Ser. No. 09/459,058, filed Dec. 11, 2000, which are incorporated by reference as though set forth in full and include the same inventors as the present application, disclose a radio-frequency or microwave-energy based catheter for ablating biological tissues within the body vessel of a patient. The catheter has a proximal portion, a distal portion with a distal end and a lumen extending from the proximal portion to the distal portion. The catheter incorporates an elongated catheter guide that is located within the catheter lumen and is secured to the distal portion of the catheter at one end, with the other end portion extending proximally within the catheter lumen to be coupled to a positioning mechanism. A significant advantage of the catheter guide is that it is deployable beyond the distal end of the catheter to form a loop, which is conformable to the interior contour of the body vessel. The catheter guide carries the catheter with a radio-frequency or microwave energy based antenna incorporated at the distal portion of the catheter. The antenna includes a helical coil, which accommodates the catheter guide passing through it.

The radio-frequency antenna is adapted to receive and irradiate radio-frequency energy in the microwave range at a frequency typically greater than 300 Megahertz (MHz) in the electromagnetic spectrum for ablating biological tissue along a biological ablation pathway.

SUMMARY OF THE INVENTION

The catheter of the present invention provides further enhancements and features to the catheter described in U.S. Pat. No. 6,190,382 and U.S. patent application Ser. No. 09/459,058. These improvements and features, among others, include a shapeable antenna, various pre-shaped antennas at the distal ends, tendon-type antenna deflecting and steering mechanisms for easy deflection, steering and manipulation of the catheters, and sensors for monitoring different parameters during ablation.

The shapeable antenna of the present invention allows for precise ablation of body tissue, and is particularly suitable to create transmural linear or curvilinear ablation lesions on the inner surface of the atrium. These lesions can then act as barriers to the conduction of electrical impulses, thus preventing atrial fibrillation. The shapeable antenna apparatus allows the antennas to quickly, easily, and precisely achieve optimum position over a target tissue and maintain stability while RF energy is being applied to the target tissue to bring about therapeutic effects.

Another aspect of the invention involves a shapeable curvilinear radio-frequency antenna apparatus for ablating biological tissue within the body vessel of a patient. The shapeable curvilinear radio-frequency antenna apparatus includes a flexible catheter body including a distal portion and an elongated lumen, inner and outer coaxially aligned conductors extending within the catheter and coaxial with the lumen, a flexible curvilinear radio-frequency antenna carried by the distal portion of the flexible catheter body in electrical communication with the inner and outer coaxially aligned conductors and adaptable to receive and transmit radio-frequency energy for ablating biological tissue, a pre-shaped deflection member carried by the flexible curvilinear radio-frequency antenna adaptable to take a pre-shaped memory curvilinear configuration, and a deflection regulating member operatively associated with the pre-shaped deflection member for regulating the deflection of said pre-shaped deflection member. At least one of the pre-shaped deflection member and the deflection regulating member is controllable for changing the configuration of the flexible curvilinear radio-frequency antenna between a straight configuration and a pre-shaped memory curvilinear configuration.

An additional aspect of the invention involves a method of ablating biological tissue within the body vessel of a patient. The method includes the steps of: providing a shapeable curvilinear radio-frequency antenna apparatus for ablating biological tissue within the body vessel of a patient, the shapeable curvilinear radio-frequency antenna apparatus including a flexible catheter body having a distal portion and an elongated lumen; inner and outer coaxially aligned conductors extending within the catheter and coaxial with the lumen; a flexible curvilinear radio-frequency antenna carried by the distal portion of the flexible catheter body in electrical communication with the inner and outer coaxially aligned conductors and adaptable to receive and transmit radio-frequency energy for ablating biological tissue; a pre-shaped deflection member carried by the flexible curvilinear radio-frequency antenna adaptable to take a pre-shaped memory curvilinear configuration; a deflection regulating member operatively associated with the pre-shaped deflection member for regulating the deflection of said pre-shaped deflection member; delivering the shapeable curvilinear radio-frequency antenna apparatus to a targeted body tissue ablation site within the body vessel of a patient; controlling at least one of the pre-shaped deflection member and the deflection regulating member to change the configuration of the flexible curvilinear radio-frequency antenna from a straight configuration to a pre-shaped memory curvilinear configuration so that the flexible curvilinear radio-frequency antenna is adjacent to the body tissue to be ablated; and ablating the body tissue using the flexible curvilinear radio-frequency antenna.

A further aspect of the invention involves a radio-frequency-based catheter system for ablating biological tissues within the body vessel of a patient. The radio-frequency-based catheter system includes a catheter with a proximal portion, a distal portion having a distal end and a lumen extending from the proximal portion to the distal portion. Inner and outer coaxially aligned conductors extend within the catheter and are coaxial with the lumen. A deflectable catheter guide is disposed within the catheter lumen and extends proximally within the catheter lumen and terminates distally of the distal end of the catheter to define a biological ablation pathway. A radio-frequency antenna is disposed at the distal portion of the catheter and is in electrical communication with the inner and outer coaxially aligned conductors. The radio-frequency antenna is adaptable to receive and transmit radio-frequency energy for ablating biological tissue along the ablation pathway.

A still further aspect of the invention involves a method of ablating biological tissue within the body vessel of a patient. The method includes the steps of providing a radio-frequency-based catheter for insertion into the body vessel of the patient, the catheter having a proximal portion, a distal portion with a distal end and a lumen extending from the proximal portion to the distal portion; inner and outer coaxially aligned conductors extending within the catheter and coaxial with the lumen; a deflectable catheter guide disposed within the catheter lumen extending proximally within the catheter lumen and terminating distally of the distal end of the catheter to define a biological ablation pathway, the catheter guide including a distal end; and a radio-frequency antenna disposed at the distal portion of the catheter in electrical communication with the inner and outer coaxially aligned conductors and being adaptable to receive and transmit radio-frequency energy for ablating biological tissue along the ablation pathway; delivering the catheter guide and the radio-frequency antenna of the catheter to a targeted body tissue ablation site within the body vessel of a patient; positioning the radio-frequency antenna of the catheter adjacent to the body tissue to be ablated by anchoring the distal end of the catheter guide in the body vessel and deflecting the catheter guide so that the radio-frequency antenna of the catheter is adjacent to the body tissue to be ablated.

Further objects and advantages will be apparent to those skilled in the art after a review of the drawings and the detailed description of the preferred embodiments set forth below.

BRIEF DESCRIPTION OF THE DRAWINGS

FIGS. 1A and 1B are side-elevational views of a RF ablation catheter including a handle with an embodiment of a steering mechanism for steering a shapeable antenna apparatus of the present invention.

FIGS. 2A and 2B are side-elevational views of a RF ablation catheter including a handle with an alternative embodiment of a steering mechanism for steering a shapeable antenna apparatus of the present invention.

FIGS. 3A and 3B are side-sectional views of an embodiment of a shapeable antenna apparatus of the present invention in a straight configuration and a shaped configuration.

FIGS. 4A and 4B are side-sectional views of an alternative embodiment of a shapeable antenna apparatus of the present invention in a straight configuration and a shaped configuration.

FIGS. 5A and 5B are side-sectional views of another embodiment of a shapeable antenna apparatus of the present invention in a straight configuration and a shaped configuration.

FIGS. 6A and 6B are side-sectional views of a further embodiment of a shapeable antenna apparatus of the present invention in a straight configuration and a shaped configuration.

FIGS. 7A–7C are alternative embodiments of the pre-shaped deflection member and the deflection regulating member of the embodiments of the shapeable antenna apparatus illustrated in FIGS. 5A,B and 6A,B.

FIGS. 9A and 9B are side-sectional views of the shapeable antenna apparatus of the RF ablation catheter illustrated in FIG. 8.

FIG. 10 is a perspective view of a radio-frequency catheter with deflectable and steering capabilities according to an embodiment of the present invention.

FIG. 11A is a partial side sectional view of the distal portion of the radio-frequency catheter of FIG. 10 and illustrates an embodiment of a deflectable catheter guide.

FIG. 11B is a cross-sectional view taken along lines 11B–2B of FIG. 11A.

FIG. 11C is a cross-sectional view taken along lines 11C—11C of FIG. 11A.

FIG. 20A is a partial top view of another embodiment of a deflectable catheter guide with bidirectional deflection capability.

FIG. 20B is a partial elevational view of the same embodiment of the deflectable catheter guide of FIG. 20A.

FIG. 20C is a cross-sectional view of the deflectable catheter guide of FIG. 20A taken along lines 20C—20C of FIG. 20A.

DETAILED DESCRIPTION OF PREFERRED EMBODIMENTS

Figure 8:
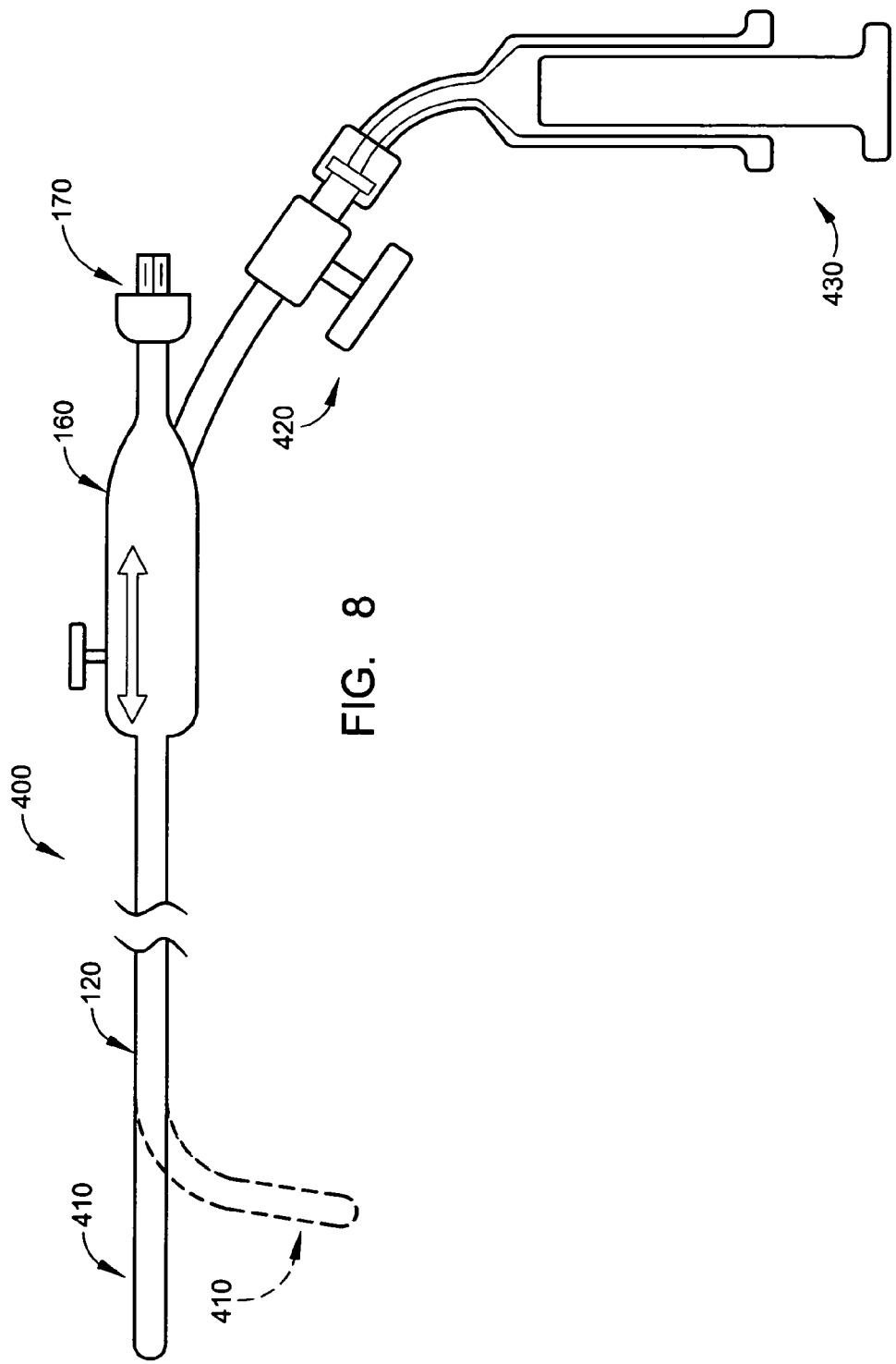
FIG. 8 is a side-elevational view of a RF ablation catheter including a shapeable antenna apparatus constructed in accordance with another embodiment of the present invention.
Figure 12A:
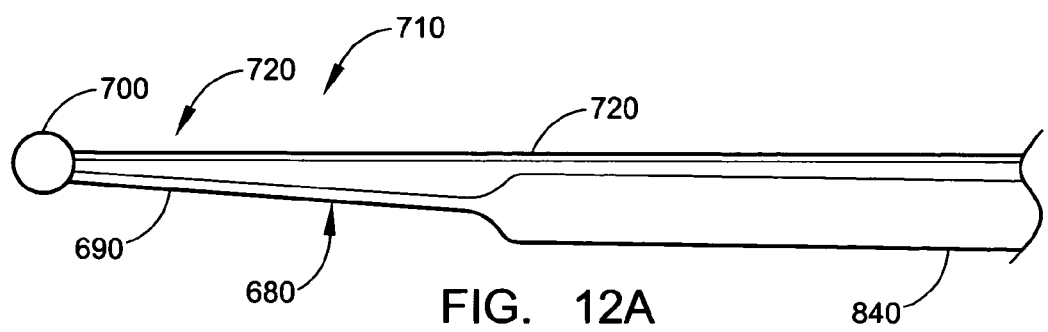
FIG. 12A is a partial elevational view of another embodiment of a deflectable catheter guide where the catheter guide has a varying dimensioned spine.
Figure 12B:
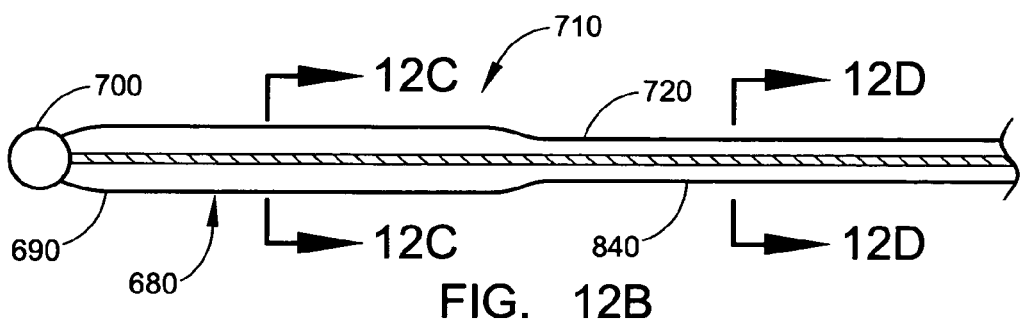
FIG. 12B is a partial top view of the same embodiment of the deflectable catheter guide of FIG. 12A.
Figure 12C:
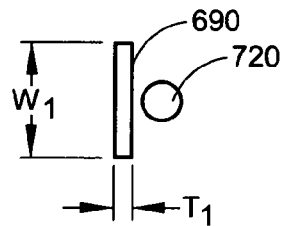
FIG. 12C is a cross-section view taken along lines 12C—12C of FIG. 12B.
Figure 12D:
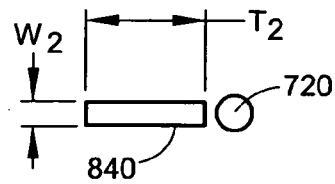
FIG. 12D is a cross-section view taken along lines 12D—12D of FIG. 12B.

With reference to FIGS. 1A and 1B, a radio-frequency ("RF") ablation catheter 100 including a shapeable antenna apparatus 110 constructed in accordance with an embodiment of the present invention is shown. The catheter 100 is adaptable for insertion into a body vessel of patient and the shapeable antenna apparatus 110 includes a radio-frequency antenna for delivering electromagnetic energy to a treatment site. The catheter 100 will first be described before describing the shapeable antenna apparatus of the present invention.

The catheter 100 has a flexible elongated tubular body 120 with a proximal portion 130 and a distal portion 140. One or more intracavity lumens 150 (FIGS. 3A, 3B) extend from the proximal portion 130 of the catheter 100 to the distal portion 140. Located at the proximal portion 130 of the catheter 100 is a handle chassis 160 for housing necessary steering and positioning controls, as will be described in further details below. Incorporated at a proximal end 160 of the catheter 100 is a coupling 170 for connecting the catheter 100 to one or more electronic devices such as a RF generator and controller (not shown) in support of the ablation procedure.

The dimensions of catheter 100 are adapted as required to suit the particular medical procedure, which are well known in the medical art. In a preferred embodiment, the catheter 100 is used to ablate cardiac tissue; however, the catheter 100 may be used to ablate other types of body tissue. The tubular body 120 of the catheter may be generally constructed of a polymer material that is bio-compatible within the body vessel environment. Examples of these materials include, but not by way of limitation, Pebax from Autochem Germany, polyethylene, polyurethane, polyester, polyimide and polyamide, with varying degrees of radiopacity, hardness and elasticity.

The catheter 100 may be formed with a plurality of segments using one or more of the aforementioned materials such that the catheter body 120 is progressively more flexible toward its distal end. The segments may be joined together by thermal bonding, butt joint, or adhesive bonding. Braiding reinforcement can also be added to the circumferential surface of tubular body 120 to attain the desirable level of stiffness and torsional strength for the catheter 100. This allows the catheter 100 to advance and negotiate through the body vessel of a patient, and to enable torque transfer along the length of the catheter from the proximal portion to the distal portion.

With reference additionally to FIGS. 3A, B, the distal portion 140 of catheter body 120 may include a softer polymer compound than the proximal portion 130, with little or no braiding, to provide the desired flexibility to accommodate distal deflection and shaping of the shapeable antenna apparatus 110. Deflection and shaping of the shapeable antenna apparatus 110 may be implemented through the use of a pre-shaped deflection member 180 and a deflection regulating member 190. The pre-shaped deflection member 180 and/or the deflection regulating member 190 may extend from the handle chassis 160 to the distal portion 140 of the catheter body 140.

The pre-shaped deflection member 180 and/or the deflection regulating member 190 may be proximally fastened to deflection control grip or thumb slide 200 (FIGS. 1A, 1B), which may be slidably engaged along a axial slot of the handle chassis 160. Axial movement of the thumb slide 200 along the axial slot, together enables a physician to shape or deflect the shapeable antenna apparatus 110 between a straight configuration (FIG. 1A) and a deflected, shaped configuration (FIG. 1B), or any configuration therebetween. A frictional capture mechanism (not shown) may be incorporated in the thumb slide 200 to maintain the grip position in the axial slot. Many such means are commercially available. Examples of such means include set-release, pressure switch or self-locking mechanisms.

FIGS. 2A and 2B illustrate a RF ablation catheter 210 similar to the RF ablation catheter 100 described above, but with an alternative embodiment of a deflection control mechanism 220 for shaping or deflecting the shapeable antenna apparatus 110. The deflection control mechanism 220 may include a rotatable collar 230 that circumferentially surrounds and is rotatably coupled to a handle shaft 240 of the handle chassis 160 to control axial movement of the pre-shaped deflection member 180 and/or the deflection regulating member 190. The handle chassis 160 may house a translation mechanism that translates rotation movement of the collar 230 to axial movement of the pre-shaped deflection member 180 and/or the deflection regulating member 190. Rotational movement of the collar 230 relative to the handle shaft 240 enables a physician to shape or deflect the shapeable antenna apparatus 110 between a straight configuration (FIG. 2A) and a deflected, shaped configuration (FIG. 2B), or any configuration therebetween.

With reference to FIGS. 3A and 3B, an embodiment of the shapeable antenna apparatus 110 will now be described in more detail. The distal portion of the catheter body 140 includes a RF antenna 250 having a flexible, helically coiled radiating antenna element 255 for body tissue ablation. In a representative embodiment, the RF antenna 250 includes an electrically conductive material or wire strip that is wound in a helical fashion to form a flexible, helical coil winding. The appropriate diameter, pitch and length of the coil winding, and the selection of the conductive material or wire strip are a matter of design choice, which can vary according to the particular procedure and flexibility requirements.

The RF antenna 250 is adapted to receive and radiate electromagnetic energy from a source of radio-frequency energy (not shown). An example of suitable spectrum of radio frequency is that of the microwave frequency range typically above 300 MHz. The RF antenna 250 is capable of applying substantially uniformly distributed electromagnetic field energy along the RF antenna 250, which is independent of the contact between the RF antenna 250 and the tissue to be ablated. The electromagnetic field transmitted is substantially normal to the longitudinal axis of the RF antenna 250, and therefore producing a uniform energy field circularly about and bounded by the RF antenna 250.

The RF antenna 250 may be in electrical contact with one or more electrical conductors 260, which in turn may be electrically coupled to a source of RF energy. The one or more electrical conductors 260 may, for example, but not by way of limitation, be made of a flexible mesh or braided wired construction, or made of a thin-film electrically conductive material, which extends proximally from the RF antenna 250 to the handle chassis 160. As described in detail below with respect to FIGS. 11A–11C, the one or more conductors 260 preferably include elongated, coaxial, circumferentially aligned inner conductor 640 and outer conductor 660. The inner conductor 640 may include or circumferentially surround a coaxial sleeve 630. An inner surface of the sleeve 630 defines the lumen 150.

The RF antenna 250 and the one or more electrical conductors 260 may be coated with a polymeric dielectric encapsulant, coating, or layer along their length to ensure their structural integrity, to protect the same from the biological environment, to isolate electrical components, and to help confine the electromagnetic field to outside of the shapeable antenna apparatus 110. The encapsulant, coating, or layer may be made of suitable materials such as silicon or polymer-based materials or rubber compounds.

The deflection regulating member 190 may be a sheath that is coaxial with and slidably mounted over the pre-shaped deflection member 180. The deflection regulating member 190 preferably has an elongated, straight tubular configuration and may be made of a plastic or metal flexible material. The deflection regulating member 190 may be pre-shaped to a desired configuration.

The pre-shaped deflection member 180 may be an elongated, flexible wire or spine that is pre-shaped to a desired configuration. The pre-shaped deflection member 180 may be made of metallic materials (e.g., bi-metal or shape-memory alloy ("SMA") materials) or polymeric materials having appropriate degree of memory, biocompatibility, and spring-like structural properties. Examples of such materials include, but not by way of limitation, nickel-titanium (sold under the trademark nitinol), stainless steel, polyamide and polytetrafluroethylene ("PTFE"). Metallic materials used can also be heat treated or cold worked as necessary to provide the desirable structural properties, such as stiffness and flexibility. Only a distal portion 270 or the entire pre-shaped deflection member 180 may be pre-shaped or made of a pre-shaped material. Use of pre-shaped materials enables pre-shaping of the deflection member 180 or deflection regulating member 190 to conform the shapeable antenna apparatus 110 to the desired linear or curvilinear profile, thus, facilitating optimal configuration and placement of the shapeable antenna apparatus 110 along the internal contour or geometry of the targeted site.

In the embodiment of the shapeable antenna apparatus 110 illustrated in FIGS. 3A, 3B, the shape of the shapeable antenna apparatus 110 is prescribed by the pre-shaped deflection member 180 by sliding the pre-shaped deflection member 180 distally out of the deflection regulating member 190 (via the deflection control mechanism at the handle chassis 160) and into the lumen 150.

Proper shaping and placement of the shapeable antenna apparatus 110 may be aided by one or more radio-opaque markers (not shown) carried by the shapeable antenna apparatus 110. With one or more radio-opaque marks, the shapeable antenna apparatus 110 becomes opaque under x-ray or fluoroscopic examination, thereby aiding the identification of its position during shaping and placement of the shapeable antenna apparatus 110 for tissue ablation.

In addition, the shapeable antenna apparatus 110 may carry one or more intracardiac electrocardiogram ("ECG") electrodes (not shown) for the physicians to obtain both optimum tissue proximity and electrical conductive activities before and after tissue ablation, as well as to obtain feedback of their actions. These electrodes may be secured along the length of the shapeable antenna apparatus 110.

With reference to FIG. 4A, an alternative embodiment of a shapeable antenna apparatus 280 is shown where, similar to FIG. 4A, the shape of the shapeable antenna apparatus 280 is prescribed by the pre-shaped deflection member 180. However, in this embodiment, the pre-shaped deflection member 180 shapes the shapeable antenna apparatus 280 to a desired configuration by slidably retracting the deflection regulating member 190 proximally off of the distal portion 270 of the pre-shaped deflection member 180. This allows the distal portion 270 to take the predetermined shape, which, in turn, causes the shapeable antenna apparatus 280 to take the desired configuration.

FIGS. 5A, 5B and FIGS. 6A, 6B illustrate further respective embodiments of a shapeable antenna apparatus 290, 300 in a straight configuration and a shaped configuration. In FIGS. 5A, 5B, the shapeable antenna apparatus 290 is similar to the shapeable antenna apparatus 110 described above with respect to FIGS. 3A, 3B in that the shapeable antenna apparatus 290 takes a desired configuration by sliding a distal portion 310 of a pre-shaped deflection member 320 axially away and distal of a deflection regulating member 330. In FIGS. 6A, 6B, the shapeable antenna apparatus 300 is similar to the shapeable antenna apparatus 280 described above with respect to FIGS. 4A, 4B in that the shapeable antenna apparatus 300 takes a desired configuration by sliding a deflection regulating member 340 axially away and proximal of a distal portion 350 of a pre-shaped deflection member 360.

With reference to FIGS. 7A–7C, a number of exemplary embodiments of the deflection regulating member 330, 340 and pre-shaped deflection member 320, 360 that may be used with the shapeable antenna apparatus 290, 300 of FIGS. 5A, 5B and FIGS. 6A, 6B are shown.

In FIG. 7A, the pre-shaped deflection member 320, 360 has a narrow generally rectangular cross-section and the adjacent deflection regulating member 330, 340 has a wider generally rectangular cross-section. In this embodiment, the pre-shaped deflection member 320, 360 and the deflection regulating member 330, 340 are parallel with each other and may be in contact with each other along their length. The pre-shaped deflection member 320, 360 and/or the deflection regulating member 330, 340 may be slidably received with a sleeve (not shown) to ensure that the deflection regulating member 330, 340 maintains the pre-shaped deflection member 320, 360 in a straight configuration (or other desired configuration) prior to shaping of the shapeable antenna apparatus 290, 300.

In FIG. 7B, the deflection regulating member 330, 340 has a generally block C-shaped cross-section and the adjacent pre-shaped deflection member 320, 360 has a generally rectangular cross-section. In this embodiment, the pre-shaped deflection member 320, 360 is slidably received by the deflection regulating member 330, 340.

In FIG. 7C, the deflection regulating member 330, 340 has a generally curved C-shaped cross-section and the adjacent pre-shaped deflection member 320, 360 has a circular cross-section. In this embodiment, the pre-shaped deflection member 320, 360 is slidably received by the deflection regulating member 330, 340.

With reference to FIG. 8, a RF ablation catheter 400 including a shapeable antenna apparatus 410 constructed in accordance with another embodiment of the invention will be described. The RF ablation catheter 400 is similar to the catheter 100 described above with respect to FIGS. 1A, 1B and 2A, 2B, except the shape of the shapeable antenna apparatus 410 is regulated by a hydraulic or pneumatic fluid pressure instead of the deflection regulating member 190. At a proximal end of the catheter 400, a stop cock 420 may be used to connect the catheter 400 to a hydraulic or pneumatic fluid pressure source 430. In the embodiment shown, the fluid pressure source 430 is a syringe filled with a fluid (e.g., saline); however, in alternative embodiments, the fluid pressure source 430 may be a pump or an alternative fluid pressure source.

With reference additionally to FIGS. 9A, 9B, a pre-shaped deflection member such as the pre-shaped deflection member 180 described above with respect to FIGS. 4A, 4B may be fully deployed or integrated into the shapeable antenna apparatus 410 so that the antenna apparatus 410 takes the shape of the pre-shaped deflection member 180 as shown in FIG. 9A. The pre-shaped deflection member 180 may be disposed in the one or more lumens 150 of the catheter 400, may be disposed in the antenna 250, may be disposed in the wall of the catheter body 120, or the catheter body 120 may be pre-shaped. To straighten the shapeable antenna apparatus 410 to the configuration shown in FIG. 9B, fluid pressure may be imparted to the interior of the distal portion 140 of the catheter 400 by the fluid pressure source 430. For example, with a valve of the stop cock 420 in an open position, the plunger on the syringe fluid pressure source may be pressed, causing fluid from the syringe to be injected into the distal portion 140 of the catheter body 120. This causes pressure to be exerted in the shapeable antenna apparatus 410 generally in the direction of the pressure arrows shown, straightening the pre-shaped shapeable antenna apparatus 410. The shapeable antenna apparatus 410 may be maintained in the straight configuration shown in FIG. 9B by closing the valve on the stop cock 420 so that fluid in the catheter body 120 does not escape the catheter body 120. To return the shapeable antenna apparatus 410 to the configuration shown in FIG. 9A, the valve on the stop cock 420 may be opened, and the plunger of the syringe fluid pressure source 430 may be withdrawn. This removes the fluid from the distal portion 140 of the catheter body 120, and the shapeable antenna apparatus 410 takes the shape of the pre-shaped deflection member. Thus, the fluid pressure in the shapeable antenna apparatus 410 serves the same function as the deflection regulating member described above, and the control of fluid pressure to the shapeable antenna apparatus (e.g., through the syringe fluid pressure source 430 and the stop cock 420) serves as a deflection control mechanism.

In another embodiment, where the pre-shaped deflection member 180 is disposed in the antenna 250, is disposed in the wall of the catheter body 120, or the catheter body 120 is pre-shaped, a deflection regulating member such as deflection regulating member 190 may be slidably received within the elongated lumen 150 for regulating the deflection of the shapeable antenna apparatus.

The shapeable antenna apparatus will now be generally described in use. The catheter is inserted through an opening into a body vessel of a patient where it is brought into the proximity of target tissue for ablation. Prior to the insertion, the shapeable antenna apparatus is provided in the straight configuration. Once inserted, the distal portion 140 of the catheter is manipulated to reach within the proximity of the location where ablation is needed. Steering of the catheter through the patient's vasculature to the target ablation site may be done using a steering assembly of the catheter, and/or, steering of the distal portion 140 of the catheter to the target ablation site may be performed using the shapeable antenna apparatus and the deflection control mechanism described above. Directional control may be accomplished with the thumb slide 200, the rotatable collar 230, or by controlling fluid pressure to the shapeable antenna apparatus (e.g., with catheter 400).

Placement, shaping, and deflection of the shapeable antenna apparatus may be facilitated by one or more radio-opaque markers placed on the distal portion 140 of the catheter. The position of the one or more radio-opaque markers may be detected by suitable x-ray or fluoroscopic means, as practiced in the art. After the distal portion 140 of the catheter is placed within the proximity of the tissue ablation site, the shapeable antenna apparatus may be shaped to a desired configuration by any of the processes described above for shaping the shapeable antenna apparatus (e.g., deploying the pre-shaped deflection member distal of the deflection regulating member so that the shapeable antenna apparatus takes the shape of the distal portion of the pre-shaped deflection member, retracting the deflection regulating member in a direction proximal of the distal portion of the pre-shaped deflection member so that the shapeable antenna apparatus takes the shape of the distal portion of the pre-shaped deflection member, releasing fluid pressure from the distal portion 140 of the catheter so that the shapeable antenna apparatus takes the shape of the distal portion of the pre-shaped deflection member). The shapeable antenna apparatus is manipulated to the desired shaped for optimal ablation of target body tissue. Alignment of the RF antenna 250 with the target ablation site may be further aided with the use of the intracardiac ECG electrodes.

By way of example, in the case of an atrium of the heart, the shape of the shapeable antenna apparatus may be adjusted to conform to the contour of the interior wall of the atrium to allow at least a portion of the shapeable antenna apparatus to rest upon the atrial wall, which establishes line contact between the atrium and the shapeable antenna apparatus. The shapeable antenna apparatus is flexible enough to allow at least a portion of the shapeable antenna apparatus to conform to the internal contour of body vessel and to rest against its internal wall. As the atrial wall pulsates, the shapeable antenna apparatus, which is in contact with the atrial wall, will also move in concert, thereby achieving an affixed and stable relationship with the location of the body vessel where treatment is desired.

Once the desired shape profile for the shapeable antenna apparatus has been acquired and aligned in parallel with the desired ablation pathway, the shape of the shapeable antenna apparatus may be secured in position (e.g., with a set-release, pressure switch, self-locking mechanism, moving the valve of the stop cock 420 to the off position). Thereafter, tissue ablation can be accomplished with the application of radio-frequency energy. Depending on the particular procedure requirements, the length of the ablation can be adjusted by positioning the RF antenna along various target tissue locations followed by applications of the RF energy. Thus, long and contiguous ablation lines can be easily established to substantially eliminate the risk of electrical impulse leakage between ablated tissue pathways.

The above may be repeated or performed for other locations within the atrium or other regions of the body as necessary depending on the particular procedure requirements.

From the above description, it is apparent that the shapeable antenna apparatus of the present invention allows the antennas to quickly, easily, and precisely achieve optimum position over a target tissue and maintain stability while RF energy is being applied to the target tissue to bring about therapeutic effects.

With reference to FIGS. 10–11C, another embodiment of a radio-frequency catheter 500 for ablating biological tissues of a body vessel, such as, but not limited to the atrium of a patient, will be described. The catheter 500 is adaptable for insertion into a body vessel and includes a deflectable catheter guide 510 that is located within a catheter lumen 520. The deflectable catheter guide 510 may be located in the catheter 500 in addition to the shapeable antenna apparatus described above. Alternatively, the catheter 500 may include the deflectable catheter guide 510, but not the shapeable antenna apparatus. A radio-frequency or microwave antenna 530 is provided at a distal portion 540 of the catheter 500. The antenna 530 receives and transmits radio-frequency (microwave) energy for tissue ablation.

The catheter guide 510 prescribes the ablation pathway of the antenna 530 for tissue ablation. In a representative embodiment of the invention, the catheter guide 510 includes elongated portions that are secured to a slide control mechanism 560 of a catheter handle 570 outside the body vessel for deflection, steering, positioning and deployment control.

A connection cable 580 extends from a proximal end 590 of the catheter handle 570 and includes an electrical connector or coupling 600 for connecting the catheter 500 to one or more integrated and/or separate electronic devices such as, but not limited to, a RF generator, an ECG system, and controller (not shown) in support of the ablation procedure.

A catheter positional control 610 may extend from the proximal end 590 of the catheter handle 570 for steering the catheter 500 through the patient's vasculature and/or for controlling axial movement of the catheter guide 510.

The RF antenna 530 may include an electrically conductive material or wire strip that is wound in a helical fashion to form a flexible, helical coil 620. The appropriate diameter, pitch and length of the coil winding, and the selection of the conductive material or wire strip are a matter of design choice, which can vary according to the particular procedure and flexibility requirements.

To enhance its shape integrity, the RF antenna 530 is provided with an inner tubing, tubular liner, or sleeve 630, which has a flexible extended body extending from the helical coil 620 proximally toward the handle 570 of the catheter 500. Sleeve 630 is constructed of a dielectric material, which reduces the likelihood of electrical short between the metallic surfaces of helical coil 620 and body fluids in the lumen 520, and to help confine the electromagnetic field to the outside of the lumen 520.

The helical coil 620 is electrically coupled to a first or inner conductor 640, which is in turn electrically coupled to a source of RF energy through the electrical coupling 600. The inner conductor 640 is made of a flexible mesh or braided wired construction, or made of a thin-film electrically conductive material, which circumscribes the outer surface of sleeve 630 and extends proximally from the helical coil 620 to the handle 570. In this embodiment, inner conductor 640 assumes an elongated tubular configuration. An inner wall of the sleeve 630 defines the lumen 520.

Inner conductor 640 is coated with a polymeric dielectric protective coating or layer 650 along its outer circumferential surface and extends proximally to the handle 570. Dielectric layer 650 serves as a substrate for a second or outer conductor 660 and electrically isolates the inner conductor 640 from the outer conductor 660.

The helical coil 620 is wound around the outer circumferential surface of the dielectric layer 650 and is electrically coupled to outer conductor 660. In turn, outer conductor 660 is electrically coupled to the source of RF energy.

In the embodiment shown, outer conductor 660 is made of an electrically conductive material circumscribing the dielectric layer 650, and extends from the helical coil 620 proximally toward the handle 570. The outer conductor 660 can be made of braided wired construction or thin film electrically conductive material.

The helical coil 620 may be coated with a polymeric dielectric encapsulant along its outer circumferential surface to ensure the structural integrity of the helical coil 620 and to protect the same from the biological environment. The encapsulant is made of suitable materials such as silicon or polymer-based materials or rubber compounds.

Similarly, an outer jacket 670 made of similar materials is provided to encase the helical coil 620 and the outer conductor 660 and to provide electromagnetic and thermal isolation from the biological environment.

Thus, the distal portion 540 of the catheter 500 includes a set of electrical conductors, each of which is formed in an elongated tubular configuration and arranged in a substantially coaxially and circumferentially aligned relationship with each other to form a hollow cable which extends from the helical coil 620 proximally to the handle 570 for the delivery of RF energy. This configuration is advantageous because the tubular conductors 640, 660 (which may be helically coiled) and the helically coiled antenna 530 maximize the electrically conductive surface area, and, hence, efficiency of the microwave energy delivery, while providing a central coaxial lumen to accommodate the catheter guide and/or shapeable antenna apparatus. Although the lumen 520 is shown coaxial with the conductors 640, 660, in an alternative embodiment, the lumen 520 may include one or more lumens, one or more of which may not be coaxial with the conductors 640, 660.

The catheter guide 510 may be longitudinally deployed from the catheter 500 within a body vessel and is flexibly conformable to the contour of the body vessel. Alignment of the catheter guide 510 with the desired tissue ablation pathway may be facilitated with the use of one or more radio-opaque markers and intracardiac electrodes mounted along the catheter guide 510. In an alternative embodiment, the catheter guide 500 may be fixed relative to the catheter 500.

The catheter guide 510 includes an elongated flexible spine 680 with a distal end portion 690 including a distal atraumatic tip 700. The distal end portion 690 may be secured to a distal portion of the antenna 530, at the distal end of the catheter 500, so that the atraumatic tip 700 is adjacent to the antenna 530. In an alternative embodiment, the catheter guide 510 may be fixed to the catheter 500 so that the atraumatic tip 700 extends a distance from the end of the catheter 500.

The tip 700 is atraumatic to reduce the potential for perforating a body vessel. Optionally, the atraumatic tip 700 is formed of radio-opaque material to support identification of the location of the antenna 530 during administration of the ablation procedure.

The spine 680 is made of one or more spring-like flexible materials. By way of examples, in one embodiment of the invention, the spine 680 is made of stainless steel. In another embodiment of the present invention, the spine 680 is constructed of a plurality of elongated members having pre-defined dimensions and joined to form a unitary body. The proximal portion of the spine 680 may be secured to the slide control mechanism 560.

In an additional embodiment of the spine 680, the distal end portion 690 of the spine 680 may be more flexible than remaining portions of the spine 680, i.e., the spine 680 may have variable stiffness along at least part of its length. This difference in flexibility can be effected by varying the shape and the size of the cross-sectional profile of the spine 680.

In a further embodiment of the spine 680, at least the distal end portion 690 of the spine 680 may be made of a bi-metal or shape-memory alloy ("SMA") material such as the nickel-titanium alloy sold under the trademark nitinol. Alternatively, the entire spine or a larger portion of the spine 680 than the distal end portion 690 may be made of such SMA material. The use of SMA material enables pre-shaping of the catheter guide 510 or distal portion 540 of the catheter 500 to conform the catheter body to attain a desired curvilinear profile, thus facilitating the navigation and placement of the catheter 500 to the internal contour or geometry of the body vessel. Means and methods for pre-shaping of SMA materials are generally known in the art and are not discussed in details here.

Figures 17A, 17B:
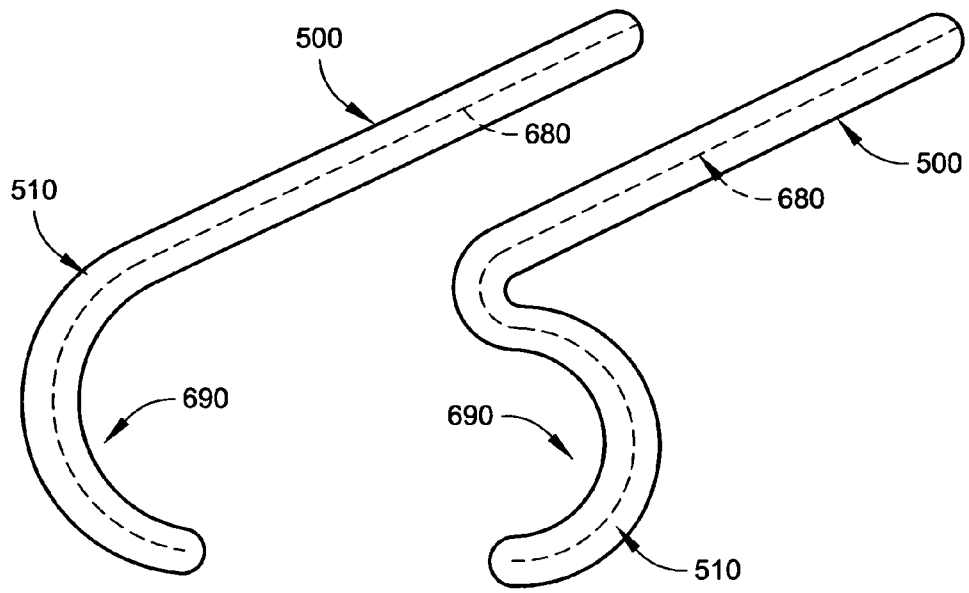
FIGS. 17A and 17B are schematic depictions of a clockwise and a counterclockwise pre-shaped distal portion of a radio-frequency catheter.

Examples of pre-shaped configurations of the catheter guide 510 in application are shown in FIGS. 17A and 17B. In FIG. 17A, the spine 680 is shown with a pre-shaped counterclockwise hook or curve. In FIG. 17B, the spine 680 is shown with a pre-shaped clockwise hook or curve.

With reference to FIGS. 12A–19, an another embodiment of a catheter guide 710 will be described. The catheter guide 710 includes a spine 680, an atraumatic tip 700, and a second elongated strip or pull wire tendon 720 that extends within the catheter lumen 520 along the length of the spine 680. The pull wire tendon 720 is constructed of elastic spring-like materials. The pull-wire tendon 720 may also be constructed of SMA materials, optionally pre-shaped to accommodate the particular geometry requirement of the internal body vessel. A distal portion of the pull wire tendon 720 is secured at the atraumatic tip 700. At this location, the distal end portion 690 of the spine 680 can also be secured. A proximal portion 730 (FIG. 19) of the pull wire tendon 720 may be secured to a thumb slide 740 of a slide control mechanism 750 via a fastener 760. The thumb slide 740 may be slidably engaged along a longitudinal slot 770 of a handle casing 780 of the handle 570. Longitudinal movement of the thumb slide 740 along the longitudinal slot 770 enables a physician to deflect the distal end portion 690 of the catheter guide. A frictional capture mechanism (not shown) may be incorporated in the thumb slide 740 to maintain the grip position in the longitudinal slot 770. Many such means are commercially available. Examples of such means include set-release, pressure switch or self-locking mechanisms.

A proximal end 790 of the spine 680 is connected to the handle 570 at electrical junction 800. The electrical junction 800 is disposed at a distal portion of an electrical conductor 810. ECG conductor 820 extends from the electrical junction 800 through the connection cable 580 for transmitting ECG signals between an external ECG system and the one or more ECG electrodes at the distal portion 540 of the catheter 500. One or more additional conductors may extend through the connection cable 580 for connecting electrical aspect of the catheter 500 to one or more external electrical systems. The connection cable 580 includes an insulating jacket 830 and terminates at electrical coupling 600 for coupling the catheter 500 to one or more external electrical systems.

With reference specifically to FIGS. 12A–14, the distal end portion 690 of the spine 680 may be more flexible than a proximal portion 840 of the spine 680. This difference in flexibility can be effected by varying the shape and/or the size of the cross-sectional profile of the spine 680. For example, the distal end portion 690 of the spine 680 may have a cross-sectional width W1 and a thickness T1, and the proximal portion 840 of the spine 680 may have a cross-sectional width W2 and a thickness T2. In the embodiment shown, the cross-sectional width W1 is wide in the distal end portion 690 and the thickness T1 is narrow in the distal end portion 690, and the cross-sectional width W2 is narrow in the proximal portion 840 and the thickness T2 is wide in the proximal portion 840. This configuration along with orienting the pull wire tendon 720 as shown, causes the distal end portion 690 of the spine 680 to have much greater flexibility than the proximal portion 840.

Figure 13:
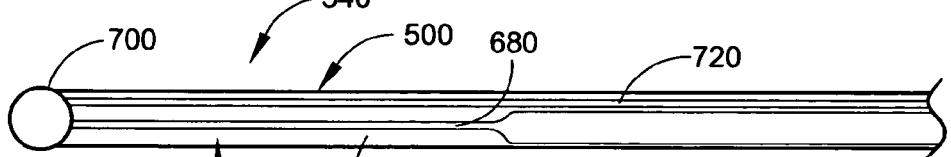
FIG. 13 is a partial elevational view of the deflectable catheter guide of FIG. 12B disposed within a lumen of a distal portion of the radio-frequency catheter of FIG. 10.
Figure 14:
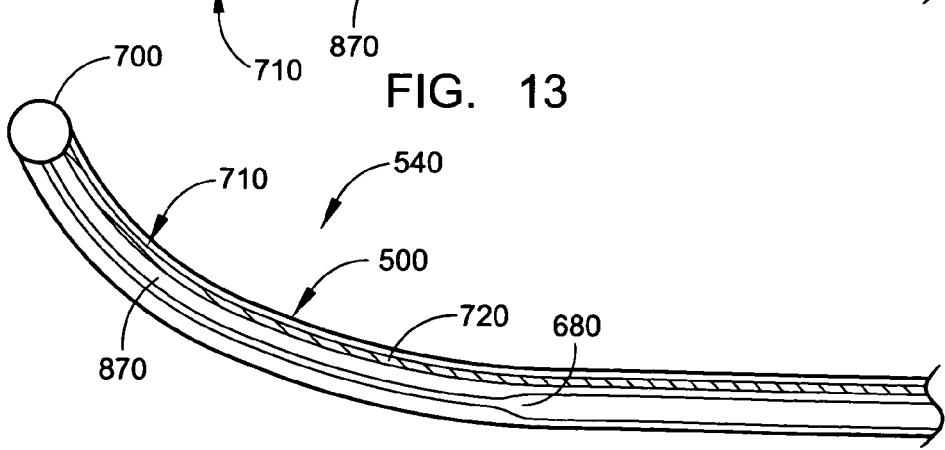
FIG. 14 is a partial elevational view of the distal portion of the radio-frequency catheter of FIG. 13 in a deflected configuration.

FIGS. 13 and 14 illustrate the distal portion 540 of the catheter 500 in a straight configuration and a deflected configuration, respectively. In the straight configuration shown in FIG. 13, the pull wire tendon 720 does not pull on the atraumatic tip 700. In the deflected configuration shown in FIG. 14, the catheter guide 710 is deflected or bent by the pull wire tendon 720 pulling on the atraumatic tip 700.

Figures 18A, 18B:
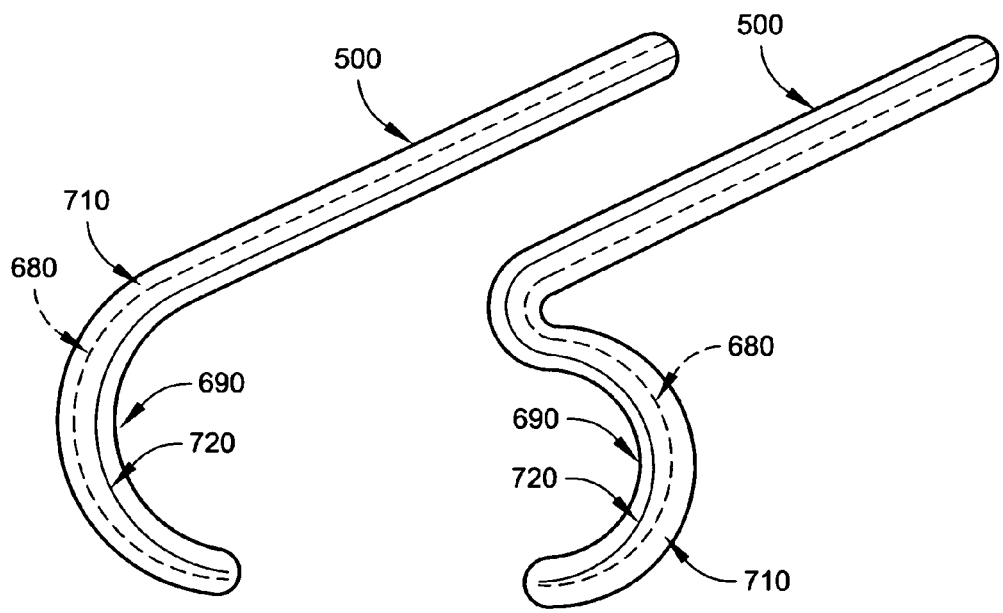
FIGS. 18A and 18B are schematic depictions of a clockwise and a counterclockwise pre-shaped distal portion of a radio-frequency catheter including a pull wire to assist in shaping the distal portion.
Figure 19:
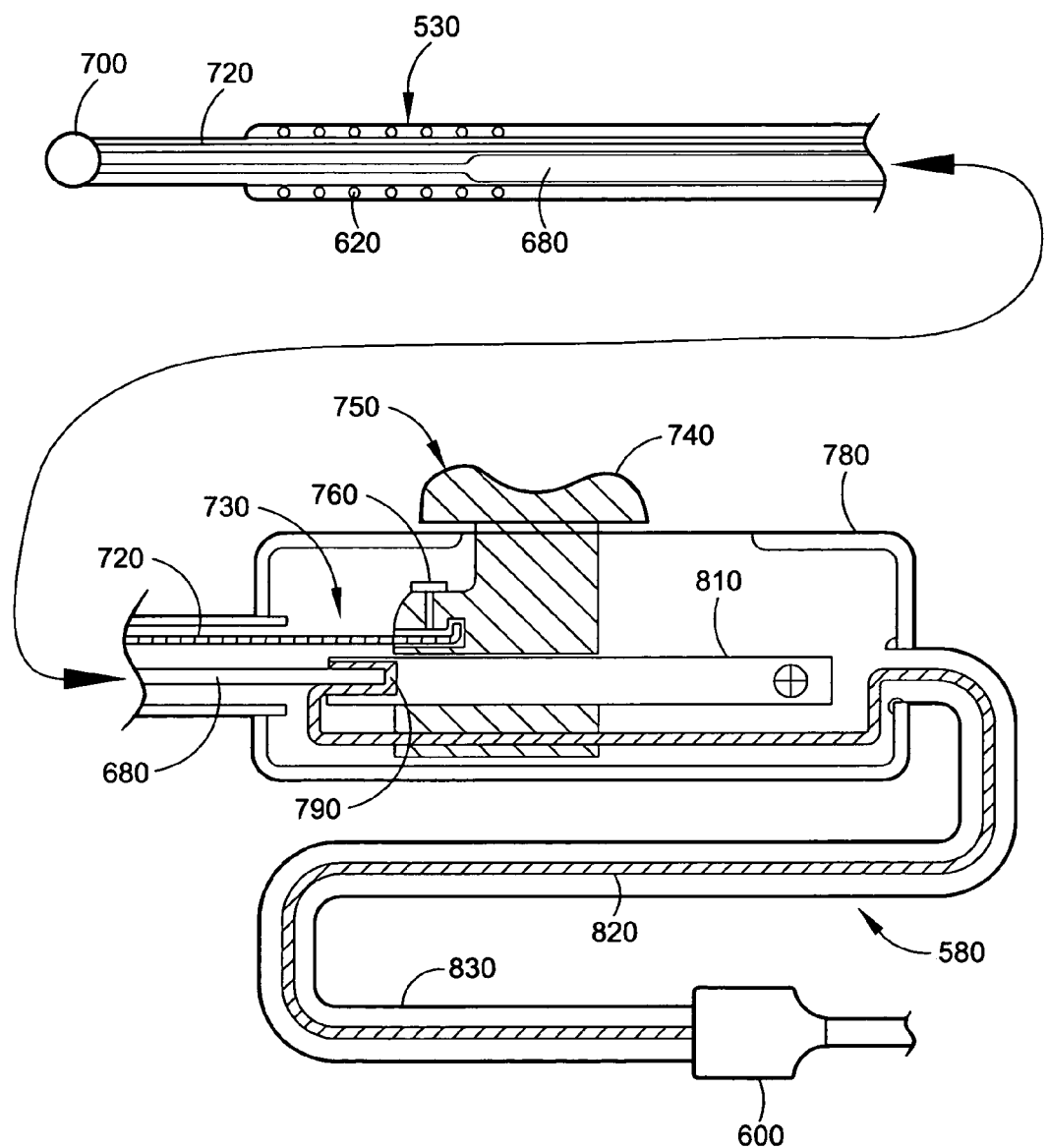
FIG. 19 is a partial side sectional view of an embodiment of a radio-frequency catheter incorporating an embodiment of a deflectable catheter guide attached to a slide control for deflection and steering of the distal portion of the radio-frequency catheter.

As discussed above with respect to FIGS. 17A and 17B, the distal end portion 690 of the spine 680 may be made of a bi-metal or shape-memory alloy ("SMA") material to enable pre-shaping of the catheter guide 710 or distal portion 540 of the catheter 500 to conform the catheter body to attain a desired linear profile. Examples of pre-shaped configurations of the catheter guide 710 in application are shown in FIGS. 18A and 18B. In FIG. 18A, the spine 680 is shown with a pre-shaped counterclockwise hook or curve. In FIG. 18B, the spine 680 is shown with a pre-shaped clockwise hook or curve. Longitudinal movement of the pull wire tendon 720 via the slide control mechanism 750 may cause the catheter guide 710 and distal end portion 690 of the catheter 500 to assume a pre-shaped configuration or a straight configuration.

Figure 15:
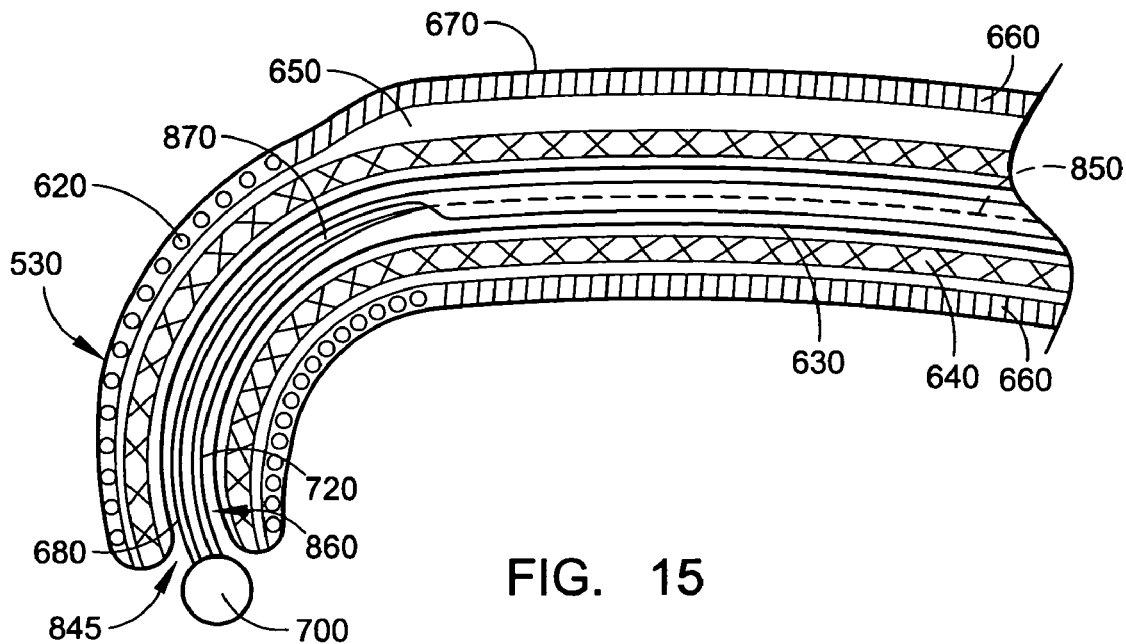
FIG. 15 is a partial side sectional view of an alternative embodiment of a distal portion of a radio-frequency catheter and shows an embodiment of a deflectable catheter guide with a flexible spine of a partial tubular construction and a pull wire tendon extending within a lumen of the flexible spine.
Figure 16:
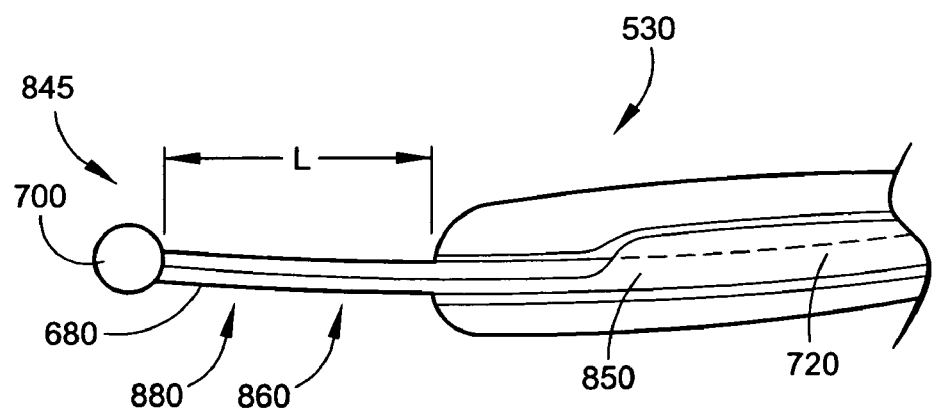
FIG. 16 is a partial side view of the distal portion of the radio-frequency catheter illustrated in FIG. 15 and shows the deflectable catheter guide with a guide leader extending distally of the distal portion of the radio-frequency catheter.

With reference to FIGS. 15 and 16, an alternative embodiment of a catheter guide 845 is shown. In this embodiment, the catheter guide 845 includes an elongated tubular body 850 that surrounds and houses the spine 680 and the pull wire tendon 740 along most or all of the length of the tubular body 850. A distal portion 860 of the elongated body 850 may have a penannular cross-section where the spine 680 and the pull wire tendon 720 are exposed. The elongated tubular body 850 includes a tubular lumen 870 that the spine 680 and the pull wire tendon 740 extend through.

In FIG. 16, a distal portion of the catheter guide 845 extends distally beyound an end of the catheter body to define a guide leader 880. The length L of the guide leader 880 may be varied depending on the particular application as defined by the relative location or distance between the RF antenna 530 and the atraumatic tip 700. The atraumatic tip 700 serves as an anchor for the catheter 500. The length L of the guide leader 880 can be predetermined and fixed during the manufacture of the catheter 500. Alternatively, the length L of the guide leader 880 may be adjustable and once the desired length L is achieved, a slide control mechanism may be locked to prevent the guide leader length L from varying. In an exemplary embodiment, the guide leader 880 has a length L of approximately 3 centimeters.

In application, the catheter guide 845 is used to establish position and contact with the surface of the body vessel. The atraumatic distal tip 700 anchors the catheter 500 (and helical antenna 530) to the body vessel with reduced risks of puncture. The flexibility of the catheter guide 845 enables it to flex to conform to the contour of the body vessel thereby securing the ablation pathway for the radio-frequency or microwave antenna 530. With the deflectable catheter guide 845 disposed within the lumen 520, the distal portion 540 of the catheter 500 conforms to the linear profile of the catheter guide 845. The pull wire tendon 720 attached to the atraumatic tip 700 of the catheter guide 845 provides further steering capability to the catheter guide 845. Manipulation of the spine 680 and the pull wire tendon 720 individually or in pair (either distally or proximally) at the slide control mechanism 750 provides further changes in the shape of the catheter guide 845 (and therefore the distal portion 540 of the catheter 500) and in directional steering. Thus, in addition to providing pre-shaping to the deflectable catheter guide 845 (and, therefore, the distal portion 540 of the catheter 500), the catheter 100 offers substantial capabilities and versatility within the body vessel.

Optionally, one or more intracardiac electrocardiogram ("ECG") electrodes may be mounted on or within the catheter guide 845 to support collection of intracardiac electrical signals when the catheter 100 is deployed.

With reference to FIGS. 20A–20C, an embodiment of a catheter guide 900 with bidirectional deflection control will now be described. The catheter guide 900 is similar to the catheter guide 710 described above, but the catheter guide 900 includes a pair of opposite pull wire tendons 930, 940 extending along the length of the catheter guide 900 to provide bidirectional deflection or steering of a spine 915 within a lumen 950. The pull wire tendons 930, 940 may be slidably disposed within elongated tendon grooves 960. Distal ends of the pull wire tendons 930, 940 may be secured to atraumatic tip 970. The spine 915 includes shaped semi-flexible spine 920 extending the majority of the length of the spine 915 and a flat flexible spine 910 that extends from a distal end 980 of the shaped semi-flexible spine 920 in a distal portion of the spine 915. The flat flexible spine 910 and the shaped semi-flexible spine 920 may be formed of any of the materials described above for the spine 680 and all other materials or combinations of materials (e.g., metals, polymers) suitable for the application described herein. Proximal ends of the pull wire tendons 930, 940 may be attached to a slide control mechanism for controlling movement of the pull wire tendons 930, 940, and, hence, deflection of the catheter guide 900.

In use, actuation of the slide control mechanism may cause one of the pull wire tendons 930 to pull on the atraumatic tip 970. This causes the spine 915 to bend or deflect in the direction of the tendon 930. Similarly, actuation of the slide control mechanism may also cause the opposite pull wire tendons 940 to pull on the atraumatic tip 970 in the opposite direction. Bidirectional deflection control of the catheter guide 900 gives the physician more control of the configuration of the distal portion of the catheter. Although unidirectional deflection control and bidirectional deflection control have been described, the catheter guide 900 may be configured for deflection control in other numbers of directions (e.g., tridirectional deflection control, etc.).

From the above description, it is apparent that the present invention not only effectively reduces, if not avoids, the need for repetitive pinpoint precision placement of an ablation catheter antenna (as was performed in the prior art), but also provides substantial navigational capabilities for deployment of the antenna 530 within the body vessel. The present invention conveniently places the radio-frequency antenna 530 along the locus of a catheter guide that defines the tissue ablation pathway. At the same time, the present invention ensures a continuous ablation pathway and substantially reduces the risk of electrical impulse leakage between ablated spots (as was performed in the prior art). Accordingly, the present invention substantially accomplishes the objective of the Maze procedure in achieving curvilinear lesions without the need for open-heart surgery. These and other aspects and advantages of the invention will become apparent from the following detailed description, and the accompanying drawings, which illustrate by way of example the features of the invention.

It will be readily apparent to those skilled in the art that still further changes and modifications in the actual concepts described herein can readily be made without departing from the spirit and scope of the invention as defined by the following claims.

What is claimed is:

1. A shapeable curvilinear radio-frequency antenna apparatus for ablating biological tissue within the body vessel of a patient, comprising:

a) a flexible catheter body including a distal portion and an elongated lumen;

b) inner and outer coaxially aligned, circumferentially spaced, longitudinally elongated conductors extending within the catheter and coaxial with the lumen;

c) a dielectrically enclosed flexible curvilinear radio-frequency antenna carried by the distal portion of the flexible catheter body in electrical communication with the inner and outer coaxially aligned conductors and adaptable to receive and transmit radio-frequency energy to apply a substantially consistently distributed electromagnetic field energy along the radio-frequency antenna for ablating biological tissue;

d) a pre-shaped deflection member carried by the flexible curvilinear radio-frequency antenna adaptable to take a pre-shaped memory curvilinear configuration;

e) a deflection regulating member operatively associated with the pre-shaped deflection member for regulating the deflection of said pre-shaped deflection member, wherein at least one of the pre-shaped deflection member and the deflection regulating member controllable for changing the configuration of the flexible curvilinear radio-frequency antenna between a straight configuration and a pre-shaped memory curvilinear configuration, wherein the deflection regulating member and the pre-shaped deflection member are relatively slidably with respect to each other in the elongated lumen.

2. The antenna apparatus of claim 1, wherein the pre-shaped deflection member is an elongated, flexible spine made of a shape-memory alloy and longitudinally disposed in the elongated lumen.

3. The antenna apparatus of claim 1, wherein the deflection regulating member is an elongated, rigid member longitudinally adjacent to the pre-shaped deflection member in the elongated lumen.

4. The antenna apparatus of claim 1, wherein the pre-shaped deflection member is movable for changing the configuration of the flexible curvilinear radio-frequency antenna between a straight configuration and a pre-shaped memory curvilinear configuration.

5. The antenna apparatus of claim 1, further including a deflection control mechanism coupled to at least one of the pre-shaped deflection member and the deflection regulating member for changing the configuration of the flexible curvilinear radio-frequency antenna between a straight configuration and a pre-shaped memory curvilinear configuration.

6. The antenna apparatus of claim 5, wherein the deflection control mechanism includes a movable control member that is rotatable to cause longitudinal movement of at least one of the pre-shaped deflection member and the deflection regulating member.

7. The antenna apparatus of claim 5, wherein the deflection control mechanism includes a movable control member that is movable in a linear direction to cause longitudinal movement of at least one of the pre-shaped deflection member and the deflection regulating member.

8. The antenna apparatus of claim 1, wherein the pre-shaped deflection member is incorporated into at least one of the catheter body and the flexible curvilinear radio-frequency antenna.

9. The antenna apparatus of claim 1, wherein the radio-frequency antenna is adaptable to receive and transmit microwave energy at a frequency greater than 300 Megahertz.

10. A method of ablating biological tissue within the body vessel of a patient, comprising the steps of:

a) providing a shapeable curvilinear radio-frequency antenna apparatus for ablating biological tissue within the body vessel of a patient, the shapeable curvilinear radio-frequency antenna apparatus including a flexible catheter body having a distal portion and an elongated lumen; inner and outer coaxially aligned, circumferentially spaced, longitudinally elongated conductors extending within the catheter and coaxial with the lumen; a dielectrically enclosed flexible curvilinear radio-frequency antenna carried by the distal portion of the flexible catheter body in electrical communication with the inner and outer coaxially aligned conductors and adaptable to receive and transmit radio-frequency energy to apply a substantially consistently distributed electromagnetic field energy along the radio-frequency antenna for ablating biological tissue; a pre-shaped deflection member carried by the flexible curvilinear radio-frequency antenna adaptable to take a pre-shaped memory curvilinear configuration; a deflection regulating member operatively associated with the pre-shaped deflection member for regulating the deflection of said pre-shaped deflection member, the deflection regulating member and the pre-shaped deflection member being relatively slidably with respect to each other in the elongated lumen;

b) delivering the shapeable curvilinear radio-frequency antenna apparatus to a targeted body tissue ablation site within the body vessel of a patient;

c) controlling at least one of the pre-shaped deflection member and the deflection regulating member by sliding at least one of the pre-shaped deflection member and the deflection regulating member relative to the other to change the configuration of the flexible curvilinear radio-frequency antenna from a straight configuration to a pre-shaped memory curvilinear configuration so that the flexible curvilinear radio-frequency antenna is adjacent to the body tissue to be ablated; and d) ablating the body tissue using the flexible curvilinear radio-frequency antenna by applying a substantially consistently distributed electromagnetic field energy to the body tissue along the radio-frequency antenna.

11. The method of claim 10, wherein the pre-shaped deflection member is an elongated, flexible spine made of a shape-memory alloy and longitudinally disposed in the elongated lumen.

12. The method of claim 10, wherein the deflection regulating member is an elongated, rigid member longitudinally adjacent to the pre-shaped deflection member in the elongated lumen.

13. The method of claim 10, wherein controlling at least one of the pre-shaped deflection member and the deflection regulating member includes moving the pre-shaped deflection member for changing the configuration of the flexible curvilinear radio-frequency antenna from a straight configuration to a pre-shaped memory curvilinear configuration.

14. The method of claim 10, further including a deflection control mechanism coupled to at least one of the pre-shaped deflection member and the deflection regulating member for changing the configuration of the flexible curvilinear radio-frequency antenna from a straight configuration to a pre-shaped memory curvilinear configuration, and the method further includes using the deflection control mechanism to change the configuration of the flexible curvilinear radio-frequency antenna from a straight configuration to a pre-shaped memory curvilinear configuration.

15. The method of claim 14, wherein the deflection control mechanism includes a movable control member that is rotatable to cause longitudinal movement of at least one of the pre-shaped deflection member and the deflection regulating member.

16. The method of claim 14, wherein the deflection control mechanism includes a movable control member that is movable in a linear direction to cause longitudinal movement of at least one of the pre-shaped deflection member and the deflection regulating member.

17. The method of claim 10, wherein the pre-shaped deflection member is incorporated into at least one of the catheter body and the flexible curvilinear radio-frequency antenna.

18. The method of claim 10, wherein the radio-frequency antenna is adaptable to receive and transmit microwave energy at a frequency greater than 300 Megahertz.

* * * * *